(12) United States Patent
Schroeder

(10) Patent No.: US 8,775,133 B2
(45) Date of Patent: *Jul. 8, 2014

(54) PERSONALIZED FIT AND FUNCTIONAL DESIGNED MEDICAL PROSTHESES AND SURGICAL INSTRUMENTS AND METHODS FOR MAKING

(71) Applicant: James Schroeder, Waukesha, FL (US)

(72) Inventor: James Schroeder, Waukesha, FL (US)

(*) Notice: Subject to any disclaimer, the term of this patent is extended or adjusted under 35 U.S.C. 154(b) by 0 days.

This patent is subject to a terminal disclaimer.

(21) Appl. No.: 13/874,948

(22) Filed: May 1, 2013

(65) Prior Publication Data

US 2013/0245801 A1 Sep. 19, 2013

Related U.S. Application Data

(62) Division of application No. 12/760,850, filed on Apr. 15, 2010, now Pat. No. 8,457,930.

(60) Provisional application No. 61/169,572, filed on Apr. 15, 2009.

(51) Int. Cl.
*G06F 17/50* (2006.01)

(52) U.S. Cl.
USPC .......................................................... 703/1

(58) Field of Classification Search
CPC .................................. A61F 2/30; G06F 19/30
USPC ............................................................ 703/1
See application file for complete search history.

(56) References Cited

U.S. PATENT DOCUMENTS

| | | | |
|---|---|---|---|
| 5,466,530 A | 11/1995 | England | |
| 5,924,862 A | 7/1999 | White | |
| 6,575,751 B1 | 6/2003 | Lehmann | |
| 6,740,054 B2 | 5/2004 | Stearns | |
| 6,916,324 B2 | 7/2005 | Sanford | |
| 7,013,191 B2 | 3/2006 | Rubbert | |
| 7,105,026 B2 | 9/2006 | Johnson | |
| 7,452,369 B2 | 11/2008 | Barry | |
| 7,581,953 B2 | 9/2009 | Lehmann | |
| 8,457,930 B2 * | 6/2013 | Schroeder | 703/1 |

(Continued)

FOREIGN PATENT DOCUMENTS

| | | |
|---|---|---|
| EP | 1574182 | 9/2005 |
| WO | 2008027549 | 3/2008 |
| WO | 2009025783 | 2/2009 |

OTHER PUBLICATIONS

Mehta, Advances in Biomedical Engineering at Ohio University: 3D Modeing and Analysis of Bones and Biomolecular Modeling, Annals of Biomedical Engineering, Blackwell Science, Inc., 1995, 3 pages, vol. 23, No. 1.

(Continued)

*Primary Examiner* — Dwin M Craig
(74) *Attorney, Agent, or Firm* — Brian S. Steinberger; Law Offices of Brian S. Steinberger, P.A.

(57) ABSTRACT

Methods, devices and systems for virtual, remote and real-time collaboration between surgeons and engineers using system learning and intelligent and timely disbursement of design and performance information to engineering teams embarking on the preliminary design event of a personalized orthopedic implant or personalize surgical instrument utilizing a case-based reasoning expert system. Additive manufacturing technology and statistically controlled advanced manufacturing processes quickly produce personalized medical devices worldwide.

19 Claims, 16 Drawing Sheets

(56) References Cited

U.S. PATENT DOCUMENTS

| | | |
|---|---|---|
| 2002/0074693 A1 | 6/2002 | Yan |
| 2002/0082741 A1 | 6/2002 | Mazumder |
| 2002/0133264 A1 | 9/2002 | Maiteh |
| 2003/0173695 A1 | 9/2003 | Monkhouse |
| 2004/0039259 A1 | 2/2004 | Krause |
| 2004/0243481 A1 | 12/2004 | Bradbury |
| 2004/0254668 A1 | 12/2004 | Jang |
| 2006/0212129 A1 | 9/2006 | Lake |
| 2007/0050074 A1 | 3/2007 | Holzner |
| 2007/0118243 A1 | 5/2007 | Schroeder |
| 2007/0276501 A1 | 11/2007 | Betz |
| 2008/0085489 A1 | 4/2008 | Schmitt |

OTHER PUBLICATIONS

Metz, et al., Hueftgelenke in 3D, F & M Feinwerktechnik Mikrotechnik Messtechnik, Hanser, Munchen, DE, 1995, pp. 580-582, vol. 103, No. 10.

* cited by examiner

PERSONALIZED FIT AND FUNCTIONAL DESIGNED MEDICAL PROSTHESES AND SURGICAL INSTRUMENTS AND METHODS FOR MAKING

This application is a Divisional Application of U.S. patent application Ser. No. 12/760,850 filed Apr. 15, 2010, now U.S. Pat. No. 8,457,930, which claims priority to U.S. Provisional Application No. 61/169,572 filed Apr. 15, 2009. The entire disclosure of each of the applications listed in this paragraph are incorporated herein by specific reference thereto.

FIELD OF THE INVENTION

The present invention provides methods, devices, systems, and instruments related to medical implants and surgical instruments produced for personalized fit and/or personalized function of individual users. In particular, embodiments of the present invention utilize a combination of medical imaging; quantitative image analysis; computer aided design, manufacturing, and engineering; telemedicine; virtual design collaboration, virtual design simulation and validation; informatics; mass-customization production; and additive manufacturing processes to personalize biocompatible devices for fit and/or function. In some embodiments, a production system is statistically controlled enabling the repeatability of the system to be probabilistically forecasted and the accuracy of features produced for medical implants and surgical instruments statistically controlled to enable mass-customization and increase speed of the overall system without jeopardizing product quality.

BACKGROUND OF THE INVENTION

Medical implants have dramatically improved the quality of life for many persons. Orthopedic devices such as total artificial hips, total artificial knees, fracture fixation plates, various fixtures, pins, wires, nails, intramedullary rods, and many others have enabled subjects to return to a high level of functioning, while restoring quality of life following debilitating diseases such as osteoarthritis, osteosarcoma, and physical trauma. Current orthopedic devices used for these and other skeletal corrections and repairs are produced in a variety of sizes to fit a range of subjects and needs. Typically the medical professional will attempt to choose the appropriate size and shape of the prosthetic device prior to surgery or intraoperatively. However, this protocol is not always successful. Often the surgeon must choose between one device that is too large, a second that is too small, and a third that is closer in size, but not quite the correct shape. Each patient has a unique need in an orthopedic device due to the infinite variation of subject anatomy combined with the infinite variation of disease and/or trauma. Although surgeons can often improvise the fit through selective removal of the subject's bone, removing otherwise healthy or undamaged tissue is not desirable, and the fit will in most cases still be less than optimal. In some cases it may be possible for the surgeon to modify the device to make a better fit, but it is not generally feasible to machine, bend, grind, drill or otherwise modify the structure of the materials used for orthopedic devices within the constraints of the operating theater. Additionally, the variety of sizes of current orthopedic devices are to accommodate different ranges of anatomical features and do not account for differences in patient activity level.

Newer methods using finite element analysis (FEA) for use in rapid prototyping have been discussed, see for example, B. V. Mehta, *Annals of Biomedical Engineering*, Blackwell Science, Inc., Vol. 23, S.1, 1995, pp. 9. While such methods discuss three-dimensional (3D) imaging of the implant site and design of an implantable device, their uses are limited to rapid prototyping and do not allow for the production of an actual prosthesis or usable article.

Johnson et al., U.S. Pat. No. 7,105,026, disclose a modular knee prosthesis. This prosthesis attempts to solve the problem of soft tissue balancing, which requires a surgical compromise to achieve a balance between flexion and extension gaps. Johnson et al. disclose a modular knee system having various distal posterior femoral components that are interchangeable so that the surgeon can choose the most correct compromise. Similarly, Sanford et al., U.S. Pat. No. 6,916,324, disclose a provisional orthopedic prosthesis for partially resected bone. Briefly, disclosed is a provisional orthopedic prosthesis having a first provisional component and a second optional component. The provisional component is used to assess the fit of a permanent prosthesis and is mounted on a partially prepared bone so as to allow a permanent prosthesis to be more accurately fitted. In both cases the final prostheses require an initial fitting or optimization of a generic prosthesis to achieve the fit of the permanent prosthesis.

Similarly, medical instruments are produced and manufactured in a series of standard sizes so as to best approximate the need of the users. In such cases the length, size and grip of an instrument are generally not available in custom sizes, personalized designs or custom alloy combinations. In such cases, the physician or end-user is limited to the best fit, weight or alloy available. In these cases, it would be helpful for the practitioner if there were medical instruments available that were a personalized fit for the size and grip of the user. Balance and weight of instruments may be controlled through internal features such as hollow, honeycomb, ribbed or a combination of these features. Such internal features have been difficult or impossible to produce before the advent of additive manufacturing technology which is incorporated into the invention.

SUMMARY OF THE INVENTION

Generally, the present invention provides systems, methods, techniques, materials and devices and uses thereof for personalized fit and/or personalized function biocompatible implants, prosthetics and interventional instruments for use in medical and veterinary applications. The devices produced according to the invention are created by referencing a patient profile (case) or, in the case of personalized surgical instruments, a surgeon profile. The devices are then produced using additive manufacturing techniques based on a computer generated model such that every prosthesis or interventional device is personalized for the fit and/or function of the user having the appropriate material composition and virtual validation of functional design for each use.

In some embodiments, design selection is based on the patient or surgeon profile in combination with historic patient or surgeon data to provide enhanced design. For example, in some embodiments, a database is interrogated to identify prior cases or profiles and their outcomes to assist in the optimization of a design for a current patient or surgeon case. Thus, the systems and methods provide for learning from historical cases and successes and challenges of variables dealt with in the past. In some embodiments, a newly defined case-based reasoning (CBR) expert system architecture will provide the engine for this invention's design optimization approach. This CBR engine will quickly enable personalized medical device designers to learn from past cases, while focusing on new variables that have not been dealt with in the past. The cycle will be repeated over hundreds of thousands of cases and the intelligence incorporated into the CBR expert system will enable medical device designers to become very accurate with features they design into implants and surgical instrumentation. Long-term successes or challenges of previous personalized medical device designs will be captured through a registry system to track patients' and surgeons' use of implants and surgical instrumentation. These data too will be available through the CBR expert system.

A unique feature of some embodiments of the invention is the use of preliminary designs based on patient profiles or surgeon profiles that permit feedback from the surgeon prior to production of the device. For example, in some embodiments, a design that incorporates patient or surgeon profile information and, optionally, historical case information, is presented to the surgeon for preliminary evaluation. The design is presented to the surgeon in a manner that permits the surgeon to evaluate the position and function of the device using 3D CAD models, as well as permitting the surgeon to observe and test performance parameters using computer simulation. The surgeon can select or recommend design changes that incorporate patient- or surgeon-specific needs based on the wisdom and experience of the surgeon and the new design can be submitted and tested, and if desired, re-evaluated prior to selecting a final design prior to release to production. In some embodiments, collaboration between the surgeon and design/production group occurs virtually, over an electronic communication network. In some embodiments, prior to device production, the surgeon engages a virtual simulation session of the surgery such that the personalized device is implanted into a virtual model of the patient.

Another unique feature of some embodiments of the invention is the use of computer assisted surgery (CAS) using robotics to assist the orthopedic surgeon in resecting the bone, eliminating sharp edges typically associated with traditional surgical approaches and producing a geometrically precise pocket or mounting surface for the device from patient specific data. For example, in some embodiments, after the surgeon has made the incision, clamped back the surrounding soft tissue and exposed the bone in preparation for the resection event, a robotic surgical system is used to create a contoured resection based on the surgeon-authorized virtual design of the device. Upon the initial resection of the bone, the robot transverses to a resting position out of the way of the surgeon. The surgeon removes the resected bone and starts the next robot sequence for removing sharp edges cases from the resection event. Once this operation is completed by the robot surgical system, the precise pocket or mounting surface for the device is created. Once the robot completes its work, it moves to a resting position out of the way of the surgeon. The surgeon, irrigates the area, vacuums the area, implants the device and closes. Prior to surgery, the robot is programmed based on the surgeon-authorized and final implant design employing patient-specific information and incorporating surgeon feedback from the preliminary design phase. In some embodiments, the surgeon controls when the robot starts and stops its work. This coordination between the surgeon and robot is enhanced by the surgeon's prior virtual surgical simulation session of the surgical procedure. In some embodiments, the robot is used principally to improve the resection process to provide precise geometries optimized for the personalized device and to avoid unnecessary removal of natural bone. In some embodiments, the surgeon preselects resection conditions, based on individual judgment, to meet the performance and lifestyle needs of the individual patient. For example, a young athlete may have different natural bone retention needs or device positioning or performance needs than an elderly person having a largely sedentary lifestyle. In some embodiments, the robotic system further is used to radius any sharp edges due to the resection process which can create problems during the rehabilitation phase for the patient. This invention is a revolutionary system of systems approach to improving the precision of the resection event and to improve the fit between the bone and implant, eliminating the need for bone cement and reducing recovery time for the patient to regain his or her previous level of functioning. From an administration perspective, the system of systems approach enables the medical institution to conduct more surgeries per day, per surgeon, while minimizing risks associated with failed surgeries requiring revision surgeries.

In some embodiments, the present invention provides a method of personalizing a biocompatible device, comprising the steps of: (a) obtaining a profile of the subject, including, for example, medical history, imaging and/or genomic data, (b) producing a virtual 3D design model, wherein the virtual 3D design model is configured to parameters from the subject profile, and (c) production of a biocompatible device, wherein the biocompatible device is configured to the physical specifications of the virtual 3D design model. In some embodiments, the present invention provides a step prior to step (a) of evaluating the subject by an orthopedic surgeon. In some embodiments, the present invention provides a step prior to step (a) of referring the subject to an orthopedic surgeon. In some embodiments, the present invention provides a step prior to step (a) of educating clinicians about the personalized biocompatible devices of the present invention. In some embodiments, the input imaging data is received from CT, MRI, PET, digital X-ray, ultrasound or other scanning of the subject. In some embodiments, the present invention provides a step following step (a) but prior to step (b) of transferring subject information to a design/design validation/production system. In some embodiments, the present invention provides generating a subject profile and case number. In some embodiments, producing a virtual 3D design model comprises calibrating, analyzing and producing a 3D CAD solid model from input imaging data. In some embodiments, producing a virtual 3D design model comprises one or more of CAD, computer aided manufacturing (CAM), FEA of biological tissue of the subject, FEA of materials, joint articulation analysis, solid modeling or 3D visualization instruments and methods. In some embodiments, producing a virtual 3D design model comprises one or more of the steps of: i) creating a 3D surface model of the bone and surrounding soft tissue/cartilage of the subject, wherein the 3D surface model is configured to the parameters from imaging of the subject, ii) creating a preliminary personalized fit and/or personalized function model, wherein the preliminary model is configured to the subject profile, and iii) designing a personalized biocompatible device, wherein the biocompatible device is configured to accurately fit the 3D surface model of the bone of the subject, subject profile variables, and quality of the preserved bone. In some embodiments, the present invention provides a step following step (b) but prior to step (c) of evaluating a virtual 3D design model. In some embodiments, evaluating the virtual 3D design model comprises performing a device simulation to analyze a virtual 3D design model. In some embodiments, the device simulation comprises a joint articulation simulation to analyze the motion of a joint by simulating the relevant daily activities of a patient or surgeon. In some embodiments, evaluating a virtual 3D design model comprises performing FEA, wherein FEA assesses function such as forces/stresses involved at the joint articulation and joint/bone interface of the personalized biocompatible device based on a subject profile. In some embodiments, evaluating a virtual 3D design model comprises performing a joint articulation simulation to validate the functioning of the device through simulated motion of the patient anatomy. In some embodiments, evaluating the virtual 3D design model comprises performing surgical simulation. In some embodiments, evaluating a virtual 3D design model comprises using a single hybrid model which includes combined and universal data sets for FEA, joint articulating simulation and surgical simulation. In some embodiments, the present invention provides a step following step (b) but prior to step (c) of offline programming a computer assisted surgery (CAS) system. In some embodiments, the present invention provides a step following step (b) but prior to step (c) further comprising verifying a CAS program using a virtual 3D model of the subject and a surgical robot. In some embodiments, the present invention provides a step following step (b) but prior to step (c) of collaboration between the surgical team and the design/manufacturing team to finalize the design of the personalized biocompatible device. In some embodiments, remote collaboration between the surgical team and the design/production team comprises reviewing and/or modifying the virtual 3D design model by the surgical team. In some embodiments, remote collaboration between the surgical team and the design/production team comprises reviewing and/or modifying said virtual 3D design model by the design/production team. In some embodiments, modifications are evaluated by FEA, joint articulation simulation, surgical simulation, and/or CAS validation. In some embodiments, the present invention provides a step following step (b) but prior to step (c) of authorizing design of the personalized biocompatible device by the surgical team. In some embodiments, the present invention provides a step following step (b) but prior to step (c) of releasing the design to production. In some embodiments, the present invention provides a step comprised of producing a 3D physical model of the biocompatible device and a 3D physical model of the bone of the subject. In some embodiments, the 3D physical model of the biocompatible device and a 3D physical model of the bone of the subject are used for surgeon and/or subject education. In some embodiments, production of the biocompatible device comprises additive manufacturing technology. In some embodiments, production of the biocompatible device comprises automated multi-axis computer numerical control (CNC) grinding and polishing of the biocompatible device. In some embodiments, the present invention provides a step following the production of the biocompatible device with one that comprises verifying surface finish and dimensional quality of the biocompatible device. In some embodiments, production of the biocompatible device comprises addition of biomaterials and/or stem cells to fight bacteria and the like and/or for tissue regeneration to the biocompatible device. In some embodiments, production of the biocompatible device comprises drug eluting functionality. In some embodiments, production of the biocompatible device comprises sterilization of the biocompatible device. In some embodiments, the present invention provides a step following step (c) of shipping the biocompatible device to the surgical team. In some embodiments, the present invention provides a step following step (c) of implanting the personalized biocompatible device into the subject. In some embodiments, implanting is performed in whole or in part by a surgeon. In some embodiments, implanting is performed or assisted by a CAS system. In some embodiments, a CAS continuously aligns to the subject's anatomical features to self-orient the positioning axes of the CAS and robot arm. In some embodiments, the present invention provides a step following step (c) of verifying the fit of the biocompatible device. In some embodiments, verifying comprises magnetic resonance imaging (MRI), nuclear magnetic resonance (NMR), digital X-ray, computed tomography (CT), ultrasound, LASER interferometry or positron emission tomography (PET) scanning of the subject. In some embodiments, the present invention provides a step following verifying data of adding the verification data to a subject profile. In some embodiments, the present invention provides a step following step (c) of rehabilitating the subject. In some embodiments, the present invention provides a step following step (c) comparing actual implantation results to results from device simulations. In some embodiments, the present invention provides a method of personalizing a biocompatible device, wherein calibrating, analyzing and producing a 3D CAD solid model from input imaging data is performed through CAD, CAM, FEA of biological tissue of the subject, FEA of materials, joint articulation simulation, solid modeling or 3D visualization instruments and methods. In some embodiments, the present invention provides a method of personalizing a biocompatible device produced by an additive manufacturing process. In some embodiments, the present invention provides a method of personalizing a skeletal orthopedic prosthesis or implant, a dental prosthesis or implant or a soft tissue or hard tissue prosthesis or implant. In some embodiments, the present invention provides a method of personalizing a biocompatible device, wherein the biocompatible device is selected from a group consisting of the following: long bones, plates, intramedullary rods, pins, total joint prosthetics or portions thereof, pelvic reconstruction prosthesis, cranial reconstruction prosthesis, maxillofacial reconstruction prosthesis, dental prosthesis, external fixation device for aligning long bones and the spine, sliding joints, overlapping plates, external or implantable orthopedic intervention prosthesis, adjustable fixtures, internal Ilizarov devices for enabling the expansion or lengthening of long bones, implantable non-orthopedic prosthesis for cardiovascular, neurological, digestive or interventional implant devices for soft or hard tissue repair, cardiovascular stents, urological stents, interventional tools, interventional guides to assist accurate preparation of the tissue to enable the proper fit of the device, and instruments for laparoscopic, interventional, radiological, and minimally invasive procedures for cardiovascular, neurological, digestive applications in soft or hard tissues. In some embodiments, the present invention provides a method of personalizing a biocompatible device manufactured from materials selected from a group consisting of Cobalt-Chromium-Molybdenum (CoCrMo) alloy, Titanium alloy, commercially pure Ti (cpTi), medical grade stainless steel, Tantalum, Tantalum alloy, Nitinol, polymers, ceramics, oxides, minerals, glasses and combinations thereof. In some embodiments, the present invention provides a method of personalizing a biocompatible device, wherein the material is selected based on desirability of biomechanical properties and interaction with surrounding biological environment of the device. In some embodiments, the present invention provides a method of personalizing a biocompatible device produced using at least two materials which are molecularly bonded through a gradient melting process sequentially, regionally or in combinations thereof. In some embodiments, the present invention provides a method of personalizing a bone prosthesis primarily consisting of Ti6Al4V ELI (body of the device) in combination with CoCrMo for the articulating function of the device using the gradient melting process. In some embodiments, the present invention provides a method of personalizing a biocompatible device, wherein the produced material is a Nitinol alloy, wherein further the device surface is substantially Ti for minimizing Ni toxicity. In some embodiments, the present invention provides a method of personalizing a biocompatible device produced by additive manufacturing technology and further produced with an element. In some embodiments, the element is a functional sensor, an optical element or a structural element. In some embodiments, the element is a MEMS lens, optical lens, ceramic whisker or a curved external fixture for Ilizarov device. In some embodiments, the present invention provides a method of personalizing a biocompatible device which has mating surfaces for joint articulation and whereby super alloys are deposited to certain regions to minimize wear of these articulating surfaces. In some embodiments, the present invention provides a method of personalizing a biocompatible device which has internal structure or surface selected from a group consisting of honeycombs, struts, ribs, hollow, solid or combinations thereof. In some embodiments, the present invention provides a method of personalizing a supporting fixture for neck or spine trauma. In some embodiments, the present invention provides a method of personalizing a cast or an articulation brace device with adjustability where range can be slowly expanded. In some embodiments, the present invention provides a method of personalizing a surgical tool that fits hand and motion mechanics. In some embodiments, the present invention provides a method of personalizing a biocompatible device, wherein the additive manufacturing process is laser additive manufacturing, laser engineered net shaping, selective laser sintering, electron-beam projection lithography, direct metal deposition or electron beam melting. In some embodiments, the present invention provides a personalizing biocompatible device produced by any of the methods described herein.

In some embodiments, medical devices are produced having a textured surface. This is particularly advantageous for orthopedic implants, as the textured surface provides sites for ingrowth of natural bone, which can stabilize the device within the bone. An advantage of such embodiments is that the use of cement or other adhesives or fillers can be avoided.

The present invention provides methods, techniques, materials, systems, and devices and uses thereof for personalizing biocompatible implants, prosthetics and interventional tools for use on medical and veterinary applications. These and other objects and advantages of the present invention will become apparent from the detailed description accompanying the drawings.

BRIEF DESCRIPTION OF THE FIGURES

Various exemplary embodiments of the methods of this invention will be described in detail, with reference to the following figures, wherein:

FIG. 3A is an MRI image of an osteosarcoma subject; FIG. 3B is a transverse section through the prospective implant site; FIG. 3C is a close up saggital view of the implant site; and FIG. 3D is a front perspective view of the cranium.

FIG. 4A is an MRI image generated showing the site for a prospective prosthesis; FIG. 4B is a planned surgical resection profile image showing the virtual fitting of the prosthesis in place; FIG. 4C shows the outline of the prospective prosthesis; and FIG. 4D represents the actual prosthesis in place.

FIG. 8A is a conventional prosthetic hip including acetabular cup and integral ball and stem; FIG. 8B is a personalized prosthetic hip with acetabular cup shaped to fit subject contours (as required due to disease, trauma, etc.), with standard integral ball and stem, and stem designed to precisely fit subjects intramedullary space, femur contours, and have a specific texture and/or material to improve bone interface; FIG. 8C is a hybrid prosthesis having a conventional prosthetic hip ball and stem but having a personalized adjustable length according to the invention.

DETAILED DESCRIPTION OF THE EXEMPLARY EMBODIMENTS

Figure 1:
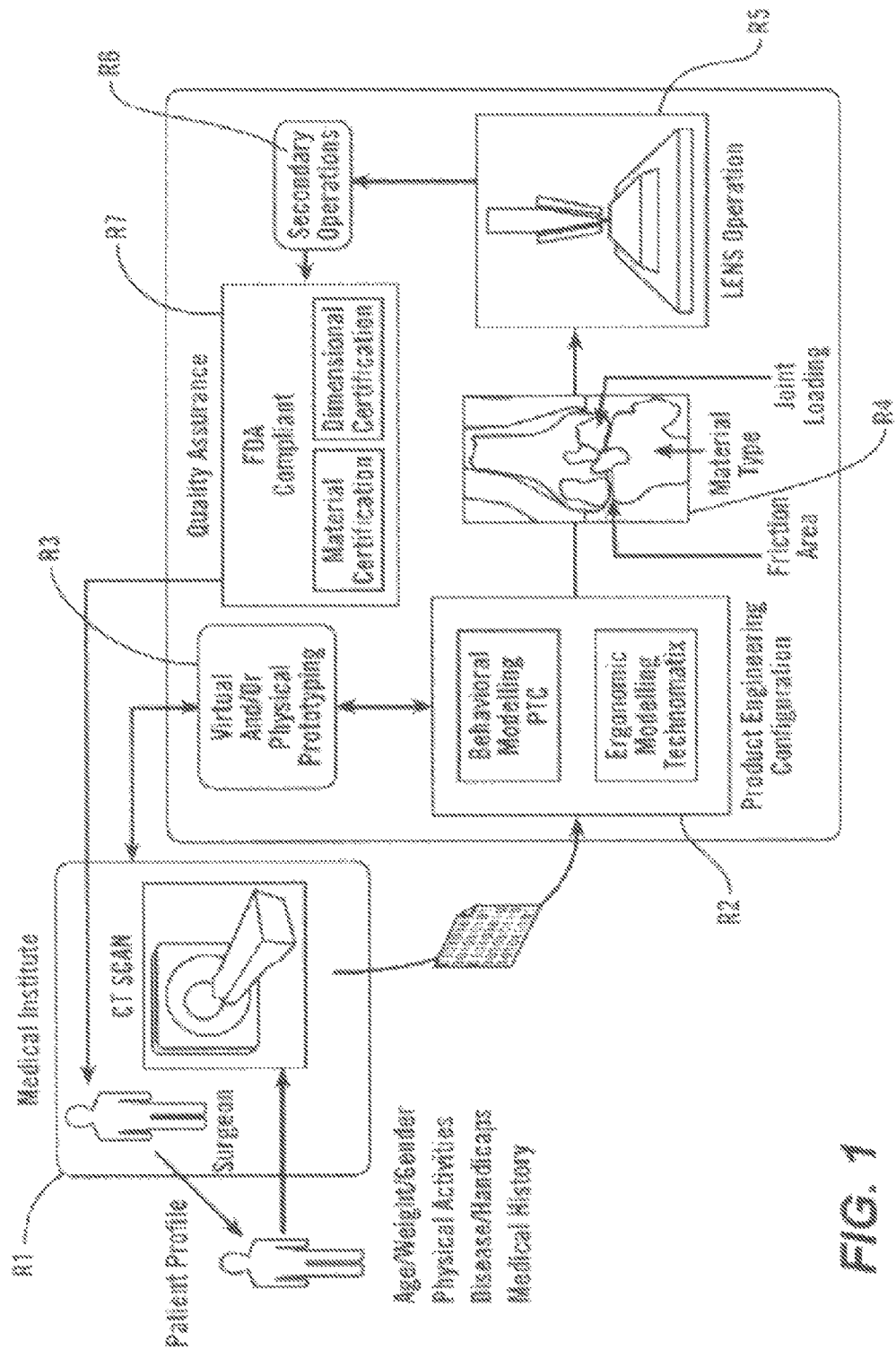
FIG. 1 illustrates a schematic of one embodiment of the present invention depicting general methodology used for creating personalized medical implants and prosthesis described in this invention (First Embodiment of invention).

The present invention provides methods, devices, systems, and instruments related to medical implants and surgical instruments produced for personalized fit and/or personalized function of individual users. In particular, in some embodiments, the present invention utilizes a combination of medical imaging; quantitative image analysis; computer aided design, manufacturing and engineering; telemedicine; virtual design collaboration, virtual design simulation and validation; informatics; mass-customization production; and additive manufacturing processes to personalize biocompatible devices for fit and/or function. This (non-prototype) production system is statistically controlled enabling the repeatability of the system to be probabilistically forecasted. The accuracy of features produced for medical implants and surgical instruments may also be statistically controlled to enable mass-customization and speed of the overall system without jeopardizing product quality.

Embodiments of the systems and methods of the present invention provide a number of unique features not present in medical practice today. Among these are a preliminary design and virtual testing phase that permits a highly validated design to be made based on patient-specific information.

Before the present methods are described, it is understood that this invention is not limited to the particular methodology and protocols described, as these may vary. It is also to be understood that the terminology used herein is for the purpose of describing particular embodiments only, and is not intended to limit the scope of the present invention.

Unless defined otherwise, all technical and scientific terms used herein have the same meanings as commonly understood by one of ordinary skill in the art to which this invention belongs. Although any methods and materials similar or equivalent to those described herein can be used in the practice or testing of the present invention, the methods and materials of some embodiments of the present invention are described herein. All publications mentioned herein are incorporated herein by reference for the purpose of describing and disclosing the devices, production methods, subjects in need, instruments, statistical analysis and methodologies which are reported in the publications which might be used in connection with the invention.

As used herein, "Subject" means mammals and non-mammals. "Mammals" means any member of the class Mammalia including, but not limited to, humans, non-human primates such as chimpanzees and other apes and monkey species; farm animals such as cattle, horses, sheep, goats, and swine; domestic animals such as rabbits, dogs, and cats; laboratory animals including rodents, such as rats, mice, and guinea pigs; and the like. Examples of non-mammals include, but are not limited to, birds, and the like. The term "subject" does not denote a particular age or sex. In some embodiments, the subject is a patient for personalized orthopedic devices or a surgeon for personalized surgical instruments.

The present invention provides methods, techniques, materials, systems, and devices and uses thereof for personalized fit and/or function biocompatible implants, prosthetics and interventional tools for use on medical and veterinary applications. The devices produced according to embodiments of the invention are created by referencing a patient profile (case) or, in the case of personalized surgical instruments, a surgeon profile. The devices are then produced using additive manufacturing techniques based on a computer generated model such that every prosthesis or interventional device is personalized for the fit and/or function of the user having the appropriate material composition and virtual validation of functional design for each use.

In some embodiments, the present invention provides a method of personalizing a biocompatible device. This method comprises the steps of (a) obtaining a profile of the subject, including, for example, medical history, imaging and genomic data, (b) producing a virtual 3D design model, wherein the virtual 3D design model is configured to parameters from the subject profile, and (c) producing a biocompatible device, wherein the biocompatible device is configured to the physical specifications of the virtual 3D design model. In this method, the device may be an implant, prosthesis or interventional tool.

In some embodiments, a potential subject for implantation of a personalized biocompatible device is referred to an orthopedic surgeon for evaluation (e.g. by another clinician). In some embodiments, a potential subject for implantation of a personalized biocompatible device is evaluated by an orthopedic surgeon (e.g. to determine if the potential subject is a candidate for a personalized biocompatible device). In some embodiments, the present invention provides educating orthopedic surgeons, physicians, nurse practitioners, nurses, and clinicians about the personalized biocompatible devices of the present invention. This education provides the user (e.g. surgeon, clinician, etc.) with the proper understanding of the personalized biocompatible devices and their advantages over other devices such that they are capable of recommending the device to potential candidates.

In some embodiments, the present invention provides collecting imaging data of a subject. In some embodiments, the imaging data is used to provide a detailed view of the subject (i.e., the particular region of interest on a subject). In some embodiments, the input imaging data may be received from MRI, NMR, digital X-ray, CT or PET scanning of the subject. In some embodiments, multiple input sources are used to provide a detailed and specific view of the region of interest. In some embodiments, subject specific parameters (e.g. measurements, dimensions, and description of the area of interest (e.g. bone break)) are derived from the imaging data. In some embodiments, parameters derived from imaging data are sufficient to define the region of interest on the subject in physical space (e.g. 3D space). In some embodiments, the imaging data is converted into a virtual model of the anatomy of the subject. In some embodiments, the imaging data and subject specific parameters derived are sufficient to create a 3D model of the area of interest on the subject (e.g. a virtual model or a physical model or the site of implantation). In some embodiments, the imaging data, subject specific parameters, subject genomic data, subject medical history, case description and/or other subject data are transferred to the design/production team. In some embodiments, a subject profile and case number are generated (e.g. based on and/or containing imaging data, subject specific parameters, subject medical history, case description and/or other subject data).

In some embodiments, a virtual 3D design model is constructed of the region of interest on the subject. In some embodiments, the virtual 3D design model comprises a three-dimensional surface model of the region of interest of the subject (e.g. bone of the subject). In some embodiments, a virtual 3D design model is constructed of the personalized biocompatible device. In some embodiments, the personalized biocompatible device is designed to fit with the existing bone of the subject. In some embodiments, the personalized biocompatible device is designed to fit with the anatomy of the subject following surgical alteration (e.g. cutting, grinding, or resection of bone etc.). In some embodiments, a preliminary exact fit model is produced (e.g. virtual model or physical model) comprising both the personalized biocompatible device and the region of interest on the subject (e.g. bone of subject and implant). In some embodiments, the methods of calibrating, analyzing and constructing the solid modeling from input imaging data is performed through CAD, CAM, FEA of biological tissue of the subject, FEA of materials, joint articulation simulation, solid modeling and/or 3D visualization instruments and related methods.

In some embodiments, a recommended resection profile (RRP) is generated of the subject. In some embodiments, one or more data sources for calculating a recommended resection profile (e.g. two data sources). In some embodiments, CAD is used to determine the geometric variance between the healthy bone and the diseased bone. In some embodiments, healthy and diseased bone involves two regions (e.g. in the exemplary the case of hemipelvectomy surgery it involves the left and right pelvises). In some embodiments, determining a recommended resection profile uses CT voxel data (e.g. to determine the manifestation of the cancerous regions of the diseased bone through comparing the healthy bone voxel density to the symmetrical cancerous bone). In some embodiments, curves from multiple data sources are combined to develop a resection profile. In some embodiments, for example, a curve identifying the geometrical differences between the healthy bone and the diseased bone is combined with a curve identifying the voxel density differences between the healthy bone and the diseased bone. In some embodiments, a plurality of data sources (e.g. curves) is merged into a single 3D non uniform rational b-spline (NURBS). In some embodiments, the present invention provides information and insight to the surgical workflow. In some embodiments, the surgeon or clinician is able to uniformly offset the recommended resection profile (RRP) by a constant amount (e.g. 1 mm, . . . , 5 mm, . . . , 10 mm, . . . , 20 mm, . . . , 50 mm, etc.) through a haptics graphical user interface, or draw on the model using a haptics joystick (e.g. to create a variable offset of the RRP based on his/her discretion).

In some embodiments, the present invention provides software packages for carrying out the steps of the invention (e.g. converting imaging data into a model, model design, evaluating a virtual model, designing a CAS protocol, carrying out CAS, collaboration, production). In some embodiments, software for the present invention is custom designed. In some embodiments, existing software and software packages can be utilized with the present invention. In some embodiments, existing software and software packages are modified or combined with custom software to suit the uses of the present invention. In some embodiments, new software is developed and combined with existing or custom software to suit the use of the present invention.

In some embodiments, a personalized biocompatible device is evaluated prior to the production of the physical device (e.g. for stability, fit, usefulness, longevity, stress to the device, stress to the bone). In some embodiments, evaluating the device comprises device simulation, FEA, joint articulation simulation, surgical simulation, CAS, etc. In some embodiments, evaluation of the device prior to production provides cost and time savings. In some embodiments, evaluation of the device prior to production provides superior results following implantation. In some embodiments, the biocompatible device is collaboratively evaluated (e.g. collaboration between the surgical team and the design/production team). In some embodiments the biocompatible device is evaluated for qualities including strength, durability, stiffness, compatibility with the anatomy of the subject, shape, joint articulation, micromotion, bacterial strain, wear, etc. In some embodiments, following evaluation, revisions are made to the design of the biocompatible device. In this case, a new virtual 3D model can be produced, tested, and re-evaluated. In some embodiments, only following approval (e.g. collaborative approval (e.g. collaboration between the surgical team and the design/production)) is a design released to the personalized biocompatible device.

In some embodiments, the systems and methods employ a database of historic intelligence to assist in design, production, and/or education. The historic intelligence, for example, includes correlations between certain patient profile information and certain design features and outcomes. Through the monitoring of multiple patients and product designs over time, patterns may be detected that permit a new patient design to be optimized using historic intelligence from prior patients that had similar characteristics and achieved desired, optimal, or non-optimal outcomes. The ability to generate and use a historic intelligence database is a unique feature of the individualized systems and methods of the present invention.

Unlike prior systems and methods, embodiments of the present invention provide preliminary design analysis that involves the treating physician, but also considers the time constraints on the surgeon. Embodiments of the present invention permit the surgeons to be presented with a preliminary design that incorporates the patient profile data, as well as, if desired, historical intelligence, and that has been validated using methods described herein to qualify the device for use in the specific patient application based on solving the patient's specific problem(s). Without these features, the ability to solve the patient-specific problem(s) is severely compromised or not possible.

In some embodiments, the personalized biocompatible device is produced by additive manufacturing process for producing the near-net-shape component and state of the art subtractive manufacturing processes for finishing the component. In some embodiments, the device may be a skeletal orthopedic prosthesis or implant, a dental prosthesis or implant or a soft tissue or hard tissue prosthesis or implant.

In some embodiments, production of the personalized biocompatible device further comprises production of a 3D physical model of the device and the implant location. In some embodiments, the physical model is produced of a different material than the final device (e.g. lighter, lower cost, and/or easier to produce material such as plastic using additive manufacturing technology). In some embodiments, 3D models are used for patient education prior to surgical implantation of the device.

In some embodiments, the biocompatible device is selected from a group consisting of the following: long bones, plates, intramedullary rods, pins, total joint prosthesis or portions thereof, pelvic reconstruction prosthesis, cranial reconstruction prosthesis, maxillofacial reconstruction prosthesis, dental prosthesis, external fixation devices for aligning long bones and the spine, sliding joints, overlapping plates, external or implantable orthopedic intervention prosthesis, adjustable fixtures, internal Ilizarov devices for enabling the expansion or lengthening of long bones, implantable non-orthopedic prosthesis for cardiovascular, neurological, digestive or interventional implant devices for soft or hard tissue repair, cardiovascular stents, urological stents, interventional tools, interventional guides to assist accurate preparation of the tissue to enable the proper fit of the device, and instruments for laparoscopic, interventional, radiological, and minimally invasive procedures for cardiovascular, neurological, digestive applications in soft or hard tissues.

In some embodiments, a biocompatible device of the present invention replaces, interacts with, facilitates the use of, restores the function or, and/or strengthens body systems, body regions and/or body parts of a subject including, but not limited to the head, mouth, neck, forehead, jaw, cheek, chin, upper limb, finger, thumb, hand, wrist, forearm, elbow, arm, shoulder, thorax, chest, rib cage, abdomen, groin, back, spine, spine components, vertebrae, sacrum, coccyx, intervertebral disks, pelvis, perineum, lower limb, hip, buttocks, thigh, knee, leg, calf, ankle, foot, toes, musculoskeletal system, bones, cartilage, ligaments, tendons, circulatory system, digestive system, endocrine system, integumentary system (e.g. skin, hair, nails, etc.), lymphatic system, reproductive system, respiratory system, and urinary system. In some embodiments, a biocompatible device of the present invention is limited to a subset of the above body systems, body regions, and body parts.

In some embodiments, the biocompatible device is produced from materials such as CoCrMo alloy, Titanium alloy, cpTi, Ti6Al4V ELI medical grade stainless steel, Tantalum, Tantalum alloy, Nitinol, polymers, ceramics, oxides, minerals, glasses and combinations thereof. Preferably, these materials are selected based on desirability of biomechanical properties and interaction with surrounding biological environment of the device.

In some embodiments, the device is produced using at least two materials which are produced sequentially, regionally, or combinations thereof. As used herein, regionally indicates a large area of the prosthesis whereas locally indicates a smaller region which is limited only be the resolution of the deposition process. In such instances different localized regions can have two or more materials in specific desired regions or location or large regions.

In some embodiments wherein two or more materials are used, the gradient of certain dissimilar materials may affect undesirable galvanic processes that can lead to corrosion or release of undesirable ions, thus such combinations are necessarily avoided.

In some embodiments, the device is a bone prosthesis and the production materials are Ti6Al4V ELI in combination with cpTi. More preferably, the production material is Nitinol alloy, such that the device surface is substantially made of Ti for minimizing Ni toxicity.

In some embodiments, the biocompatible device is produced by additive manufacturing methods. Such methods are known in the art. For example, the field of additive manufacturing is the automatic construction of physical objects using solid freeform production (SFF). SFF or additive manufacturing is a technique for producing near-net-shaped solid objects by the sequential delivery of energy and material to specified points in space to produce the solid. While the techniques of SFF share some similarities with techniques of rapid prototyping, rapid prototyping produces only a prototype typically made of plastic polymer. However, the techniques of SFF allow for the integration of more powerful methods of computer imaging and manufacturing techniques. Such techniques include, but are not limited to, laser engineered net shaping (LENS), selective laser sintering (SLS), electron-beam projection lithography (EPL), electron beam melting (EBM), and direct metal deposition (DMD). In some embodiments, LENS uses a laser to melt metal powder and deposit it on the device directly. In some embodiments LENS produces a part that is fully solid and the metal alloy composition can be dynamically changed over the volume of the device-gradient material deposition. In some embodiments, SLS utilizes a laser to fuse powdered nylon, elastomer or metal alloy. In some embodiments SLS comprises a heat treating process called bronzed infiltration to produce fully dense metal devices. In some embodiments EPL is similar to LENS and allows the device to be produced using a powdered metal alloy along the leading edge which is sintered using an electron beam instead of a laser. In some embodiments, EBM provides electrons which are emitted and projected at a powdered metal bed in which the molten metal is added layer by layer until the device is completed. In some embodiments, DMD is similar to LENS in that the desired alloy is added, in powdered form, directly to the substrate or biocompatible device and melted by a laser beam such that the device is built up layer by layer in the size, shape and particular alloy content desired. In some embodiments, DMD, EPL, LENS and EBM afford the advantage that the composition, shape and texture of the product can be changed as the device is being produced. During additive manufacturing production, the process may be programmed to pause such that an element may be added or the alloy composition changed. Then the process may be followed by continued additive manufacturing. Further, it should be appreciated that using the disclosed methods, the biocompatible device can be used such that the production materials are deposited regionally (e.g. an entire area of the implant) or locally (e.g. small areas that may be as small as the resolution of the instrumentation will allow) in some cases such area will be on the order of a few microns to tens of microns depending on the additive manufacturing process used.

In some embodiments, during production, the device is further enhanced with an element feature. Such elements may include a functional sensor, an optical element or a structural element. In some embodiments, such elements include a microelectromechanical system (MEMS) lens, optical lens, ceramic whisker or a curved external fixture for Ilizarov device or any other element that is not damaged by thermal, optical and other constraints posed by the additive manufacturing process and its resolution limits.

In some embodiments, the biocompatible device has internal structure or surface which can be solid or hollow or may include honeycomb, strut or ribbed features, or combinations thereof.

In some embodiments, the biocompatible device may be a supporting fixture for neck or spine trauma. In some embodiments, the method of personalizing a biocompatible device may be a personalized cast or an articulation brace device having adjustability such that the range of articulation can be slowly expanded. In some embodiments, the biocompatible device is a surgical tool that fits hand and motion mechanics.

In some embodiments, the invention provides a method of personalizing a biocompatible device, comprising the steps of: (a) quantitatively calibrating a medical image; (b) analyzing the calibrated medical image; (c) compiling CAD of the analyzed and calibrated medical image; (d) creating CAM from the CAD data of step (c); (e) performing FEA of biological tissues of CAM from step (d); (f) performing FEA of materials; (g) performing joint articulation simulation; (h) solid modeling using 3D visualization instrumentation and virtual reality; and (i) producing the near-net-shape device using the additive manufacturing processes. In some embodiments, the additive manufacturing process used is DMD, EPL, LENS, EBM, SLS or combinations as needed. In some embodiments, devices are produced by processes described above.

In some embodiments, the present invention comprises methods and tools to produce implantable devices that will be personally fit to the form and function of individual subjects. In some embodiments, the invention is implemented through a combination of technologies including medical imaging (including CT, MRI, PET, digital X-ray, ultrasound and others), quantitative image analysis, CAD, CAM, FEA of biological tissues, FEA of materials, joint articulation simulation, solid modeling, 3D visualization instrumentation and methods (virtual reality), and additive manufacturing process that can directly produce high strength implants from biocompatible materials with much greater structural and geometric design flexibility than conventional forging and "subtractive" machining methods. In some embodiments, the invention also comprises methods and devices for other medical devices including implants that do not require precise personalizing to subject data but nonetheless utilize the methods and tools described herein, methods to produce surgical tools and devices that are not implanted, and other related technologies that will be apparent to those skilled in the medical, material production, and other related arts.

In some embodiments, an exemplary personalized implant is generated as described below:

In some embodiments, a 3D image data of the subject is obtained with dimensionally calibrated medical imaging instrumentation such as MRI and CT, and presented for clinical evaluation. Presentation can be provided via virtual 3D display, multiple 2D sections, a solid 3D model, or a combination of these and other modalities.

In some embodiments, a clinical evaluation is made to determine the desired morphology of areas to be surgically manipulated (e.g. areas of interest, ROI) such as re-aligned or resectioned, and an initial determination is made of how an implant will be shaped to make the necessary reconstruction. Additional clinical data may also be used in this determination, as appropriate, based on the best possible medical practice.

In some embodiments, the desired shape of the implant is evaluated with respect to the intended surgical procedure based upon multiple factors. These include biomechanical FEA of tissue and FEA of implant material, mechanism for short-term and long-term tissue bonding and attachment, joint articulation simulation, desired surgical procedure, material choices, structural integrity, and the incorporation of any pre-engineered standard elements in the implant. Standard elements may include articulation components (such as the ball and socket of a prosthetic hip joint), joinery to enable multiple sections of an implant to be assembled and attached during the surgical procedure, and design features to enable the device to be adjusted in size or shape during the initial implantation and at a future time post-implantation, if desired.

In some embodiments, the above designed implant is then evaluated by a clinician using dimensionally calibrated virtual 3D presentation methods and/or solid models. Fit is checked, methods of attachment to healthy tissues are evaluated, methods of assembly of implant components (if multiple components) are evaluated, and the entire surgical procedure is performed "virtually" using 3D display and related methods and/or with solid models. In some embodiments, if required, the above steps are repeated until a final digital design and surgical plan are made.

In some embodiments, a final design of the implant is created digitally (e.g., via CAD) to precisely match the factors determined above. In some embodiments, a final design plan comprises overall shape, choice of material or materials, thickness and thickness gradients at all locations, design of internal structures such as honeycombs, struts and voids to provide ideal structural rigidity, placement of pre-engineered standard elements, surface materials (if different from bulk), surface texture, and any other necessary features. In some embodiments, the spatial resolution of the design is about 1 µm, 2 µm, 3 µm, 4 µm, 5 µm, 6 µm, 7 µm, 8 µm, 9 µm, 10 µm, 11 µm, 12 µm, 13 µm, 14 µm, 15 µm, or 20 µm to correspond with the manufacturing resolution and material handling capabilities of the direct manufacturing tooling and processes.

In some embodiments, the design created above is produced using CAM digital methods such as additive manufacturing to produce the implant with laser-based additive manufacturing technology and related methods. In some embodiments, production of each component is performed with the desired material or materials directly from powdered metals (and certain other materials) that are delivered to the desired spatial location and then laser annealed in place. This produces a very high strength fine-grain structure, enables the production of internal features, enables layers of multiple materials, gradients of material properties, inclusion of ancillary internal elements, and produces resultant structures that generally require minimal secondary machining using subtractive manufacturing technology.

In some embodiments, post-production processes are performed on the implant. Grinding and polishing may be required for joining surfaces and for bearing surfaces, such as in articulation joints. Additional processing such as ion beam implantation or annealing may be performed, as required. In some embodiments, the surface texture resolution of the laser-based additive free-form manufacturing process is about 1 µm, 2 µm, 3 µm, 4 µm, 5 µm, 6 µm, 7 µm, 8 µm, 9 µm, 10 µm, 11 µm, 12 µm, 13 µm, 14 µm, 15 µm, or 20 µm with no rough or abrupt transitions. It is thus intrinsically suitable for many tissue interfaces without further processing. In some embodiments, grinding and polishing are performed by multi-axis grinding and polishing equipment.

In some embodiments, the device is then cleaned, sterilized, packed, labeled, and shipped to the clinic for the actual surgical application as was designed for using the virtual simulation.

In some embodiments, the production of the exemplary implant above is provided as an example embodiment of the present invention and should not be viewed as limiting the scope of the present invention.

In some embodiments, the present invention can be applied to implantable and other medical devices including the following:

Implantable Orthopedic Devices:

In some embodiments, personalized implantable devices may be created for a wide variety of clinical implants including skeletal orthopedic appliances for repair of long bones (including plates, intramedullary rods, pins, and total joint prosthetics or portions thereof), pelvic reconstruction appliances, appliances for repair of cranial defects or damage, maxillofacial repairs, dental prosthetics, and others that will be apparent to those skilled in the art.

Prosthetic Devices:

In some embodiments, the methods described above may also be used for the design, development, and production of personalized devices for external fixation, such as used for aligning long bones and the spine, and for generic or non-personalized devices intended for external or implanted orthopedic intervention, and others that will be apparent to those skilled in the art.

Soft Tissue Implant Devices: In some embodiments, the methods described above may also be used for the design, development, and production of personalized and generic devices for implanted non-orthopedic applications such as for cardiovascular, neurological, gastrointestinal or other interventional implants used for soft or hard tissue repair.

Cardiovascular and Urological Stents:

In some embodiments, the methods described above may also be used for the design, development, and production of advanced devices such as geometrically complex cardiovascular and urological stents due to the unique capabilities of the design and production capabilities of this invention, and for other applications that will be apparent to those skilled in the art.

Interventional Tools: In some embodiments, the methods described above may also be used for the design, development, and production of interventional tools and instruments such as required for laparoscopic, interventional radiological, and minimally invasive procedures for cardiovascular, neurological, digestive or other applications in soft or hard tissue, and for other applications that will be apparent to those skilled in the art.

Surgical Instruments:

In some embodiments, the methods described above may also be used for the design, development, and production surgical instruments having the ergonomic and mechanical properties desired by the surgeon or other end-user to create medical and other tools that will be more comfortable, better weighted and have superior manipulating or cutting surfaces thereby providing superior performance.

In some embodiments, implantation of the personalized biocompatible device of the present invention is carried out by a surgical team (e.g. orthopedic surgical team). In some embodiments, implantation of the personalized biocompatible device makes use of CAS. In some embodiments, CAS removes and shapes the bone of the subject such that the bone provides a precise fit for the personalized biocompatible device. In some embodiments, the use of CAS by the surgical team provides precise fit of the implant with the anatomy of the subject. In some embodiments, the imaging data and modeling performed during steps of the present invention provide information required for precise CAS.

In some embodiments, a subject will require rehabilitation following implantation of the device of the present invention. Methods of post-surgical rehabilitation are well known to those of skill in the art. In some embodiments, a subject is monitored following surgery to analyze the results of the implantation (e.g. monitored for 1 year, . . . , 5 years, . . . , 10 years, . . . , 25 years, . . . , 50 years). In some embodiments, the actual implantation results are compared to device simulations performed during the implant design process. In some embodiments, differences between actual and simulated results are used in improving design software, techniques, methods, algorithms, etc.

The following examples are related to devices and methods of the present invention and are put forth for illustrative purposes only. These examples are not intended to limit the scope of the invention.

EXAMPLES

Exemplary Embodiments

This Exemplary Embodiment and Examples I through IV describe a first embodiment of the invention and examples V through XI describe a second embodiment of the invention.

As shown in FIG. 1, in some embodiments, the present invention provides methods and tools to produce implantable medical devices that will precisely fit individual subjects. The present invention also comprises medical appliances and tools and implements designed and created through the disclosed process. In some embodiments, the invention is implemented through a combination of technologies including medical imaging (including CT, MRI, PET, X-ray, ultrasound, and others) and subject consultation (R1). Next, the product engineering configuration (R2) analysis is implemented using both behavioral modeling and ergonomic modeling analysis. Next, virtual and/or physical prototyping is performed (R3) which allows for validation of the product engineering results by further reference with (R1). Then, (R4) analysis of the implant site identifies the friction area, analyzes the joint loading and identifies material types that can or should be used in production. Next, (R5) additive manufacturing is performed using, in some embodiments laser engineered net shaping. However, other methods of additive manufacturing production can be used. Then, (R6) secondary, finishing, operations are performed such as cleaning and sterilizing is performed. Then, (R7) quality assurance such as FDA compliance, material certification and dimensional certification is performed. Then, data determined in R7 is returned to the clinician confirming quality and suitability of the device and the device is implanted. As shown, quantitative image analysis, CAD, CAM, FEA of biological tissues, FEA of materials, joint articulation simulation, solid modeling, 3D visualization instrumentation and methods (virtual reality), and additive manufacturing process can directly produce high strength implants from biocompatible materials with much greater structural and geometric design flexibility than conventional forging and "subtractive" machining methods in which a larger piece of material is carved away or machined down to arrive at the product. This invention also comprises methods and devices for other medical devices including implants that do not require precise personalization to subject data but nonetheless utilize the methods and tools described herein, methods to produce surgical tools and devices that are not implanted, and other related technologies that will be apparent to those skilled in the medical and material production arts.

The following examples are provided:

| Example | Name | Description |
| --- | --- | --- |
| I | Image Acquisition and Analysis | Provides a sample scenario of steps taken within the imaging, design and collaboration portion of the process. (Primarily references FIGS. 2A and 2B Steps 1-33.) (First Embodiment) |
| II | Production | Provides a sample scenario of the steps involved in the production of the patient-specific device. (Primarily references FIGS. 2A and 2B Steps 33-35.) (First Embodiment) |
| III | Post-Production | (First Embodiment) |
| IV | Applications of Technology | Describes examples of the types of products that this invention can be used to create. |
| V | Onboard New Facilities and Clinicians | Provides a sample scenario of the steps involved in the preparation of facilities and clinicians that are new to the firm's invention so that they will be able to work with these methods, devices, systems, and instruments. (Second Embodiment) |
| VI | Provide Personalized Implant to Patient | Provides a sample scenario of the steps involved in the manufacture of personalized orthopaedic implants for specific patient anatomy and function. (Second Embodiment) |
| VII | Patient Qualification and Characterization | Describes examples of the steps taken to determine if a patient is an appropriate candidate for the devices manufactured in conjunction with this invention and the imaging work that is required in some embodiments. (Second Embodiment) |

| Example | Name | Description |
| --- | --- | --- |
| VIII | Design Patient-Specific Solution | Provides a sample scenario of the steps involved in the design of personalized orthopaedic implants for specific patient anatomy and function. (Second Embodiment) |
| IX | Pre-Surgical Collaboration | Provides a sample scenario of the steps involved in the collaborative review of the design for a personalized orthopaedic implant for specific patient anatomy and function. (Second Embodiment) |
| X | Produce Device Components | Provides a sample scenario of the steps involved in the production of personalized orthopaedic implants for specific patient anatomy and function. (Second Embodiment) |
| XI | Long-term Monitoring | Periodical updates are collected and entered in the patient registry to document success rates. The results are used by the case-based reasoning system for future improvements to design parameters. (Second Embodiment) |

Example I

Image Acquisition and Analysis

First Embodiment

Figure 2A:
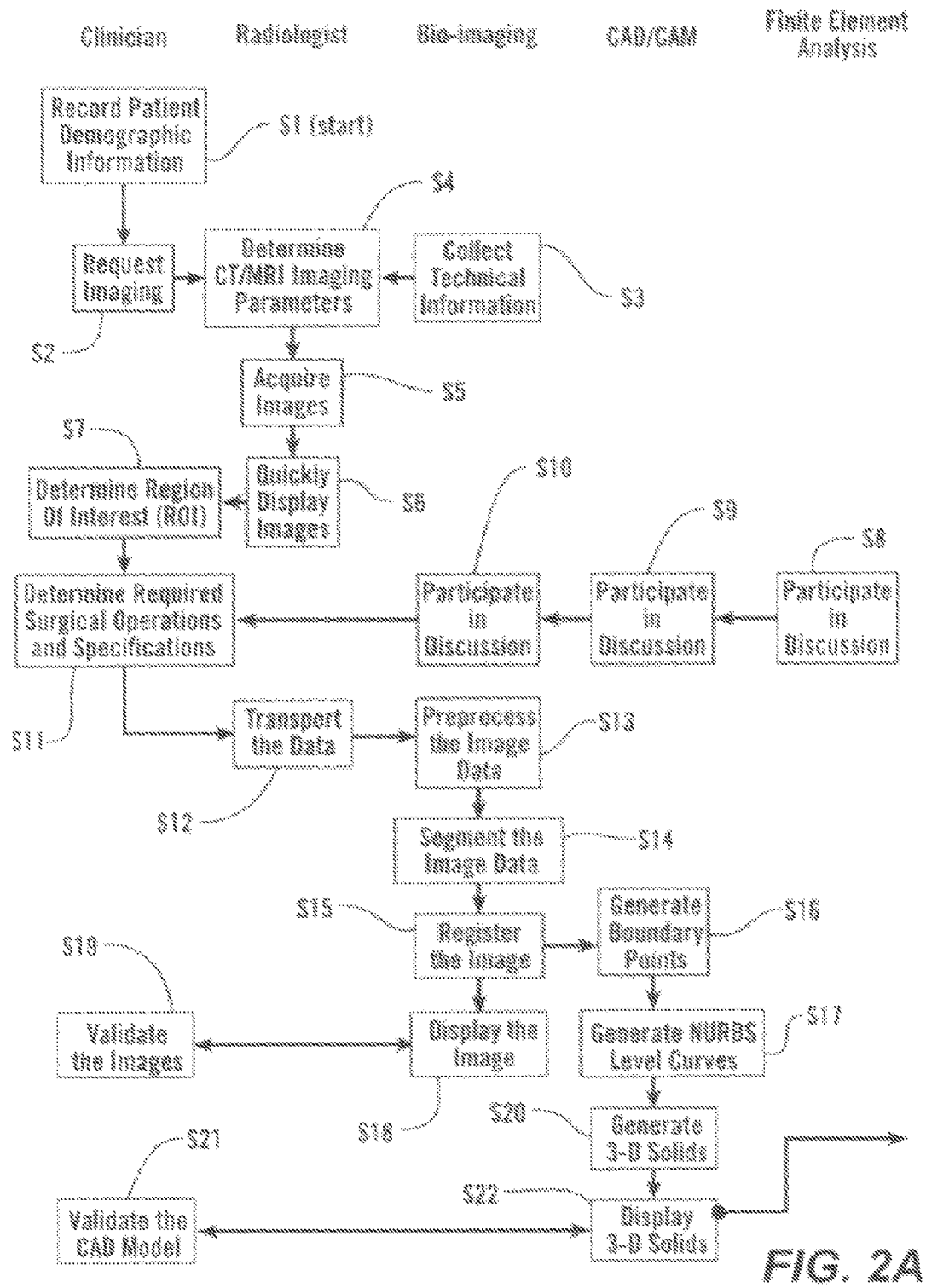
FIGS. 2A and 2B illustrate a detailed schematic of one method according to some embodiments as illustrated in FIG. 1 (First Embodiment of invention).
Figure 2B:
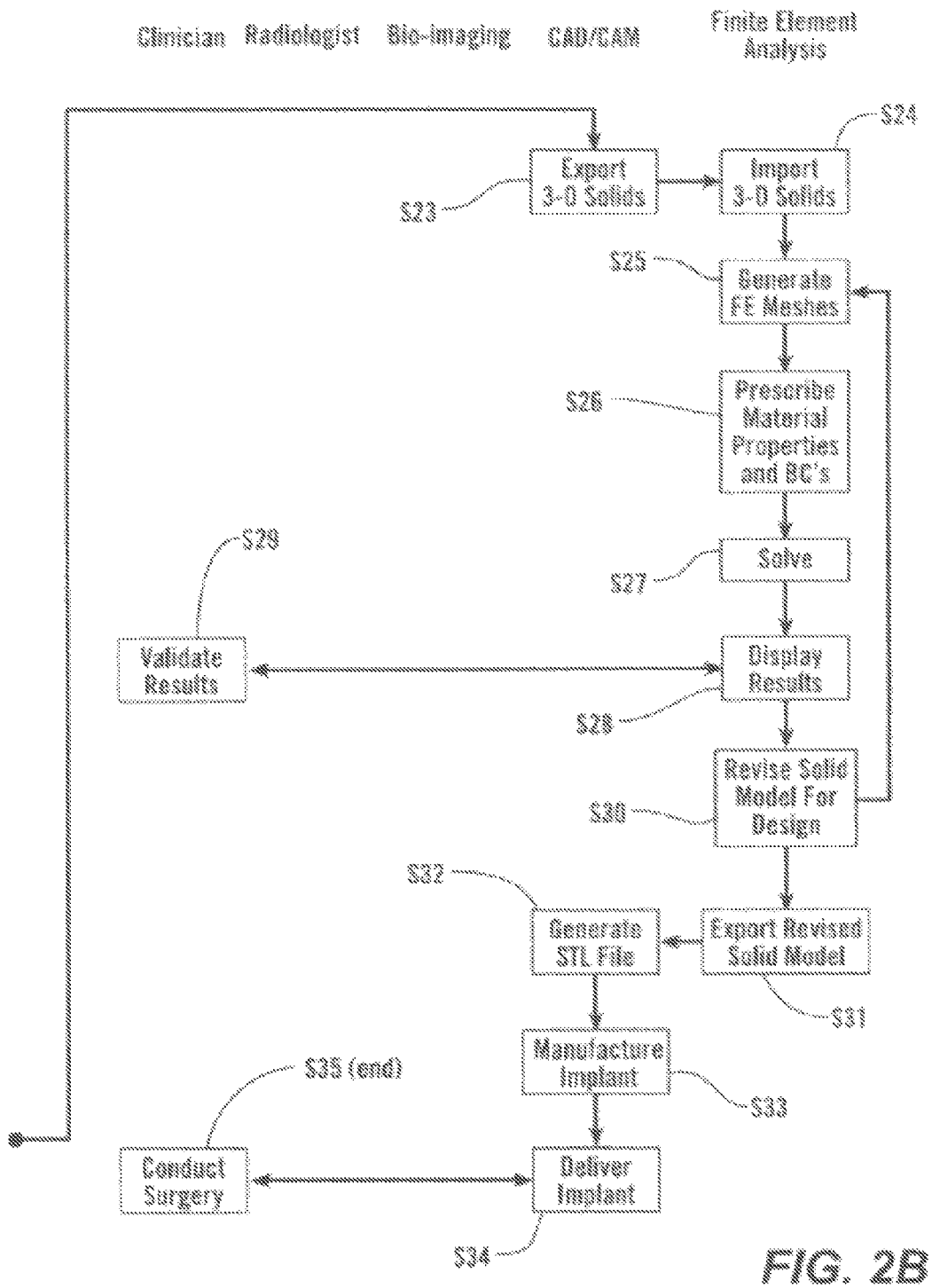
Figure 3A:
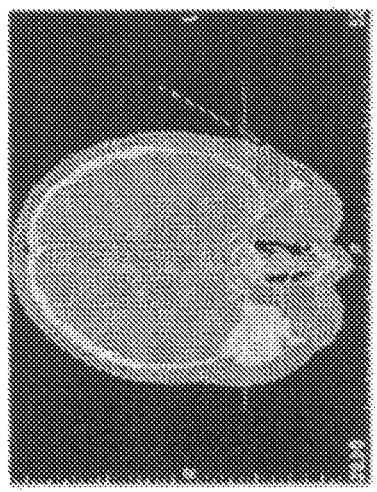
FIGS. 3A, 3B, 3C and 3D illustrate an embodiment of the present invention, wherein a series of 3D images and image reconstruction are generated from MRI images in order to provide implant devices for reconstruction of cranial defects.
Figure 3B:
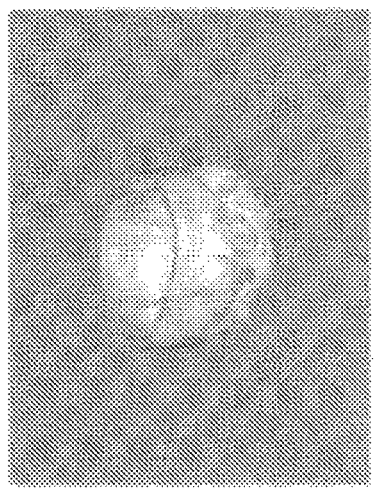
Figure 3C:
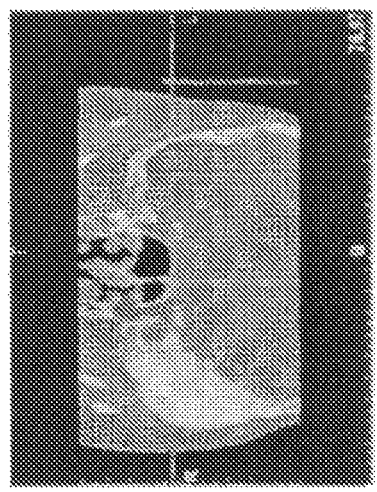
Figure 3D:
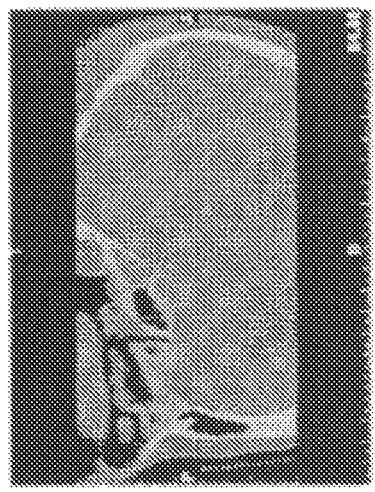
Figure 4A:
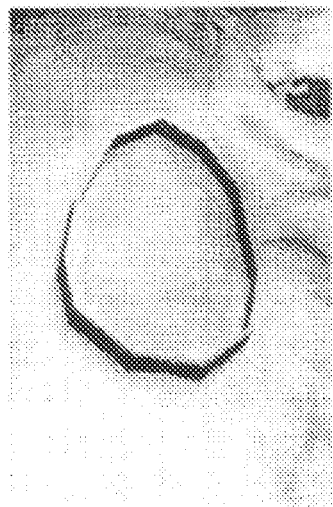
FIGS. 4A-4D illustrate an embodiment of the present invention for providing a personalized plate prosthetic for surgical repair.
Figure 4B:
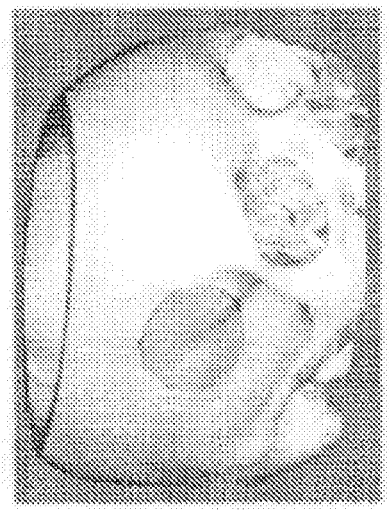
Figure 4C:
Figure 4D:
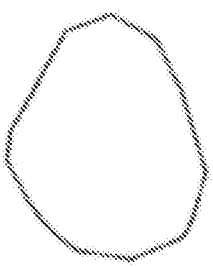

As shown in FIGS. 2A and 2B, in some embodiments, the process starts with step S1 where the subject's demographic information is recorded and the clinician makes a request for imaging, S2. 3-Dimensional image data is obtained from the subject S4 and presented for clinical evaluation with the cooperation of multiple specialists, S3 and using the invention described herein (FIGS. 1 and 2A). This uses multiple steps as listed in Table 1, and further elaborated below.

TABLE 1

Image Acquisition and Analysis

1  CT/MRI Image calibration
2  Calibration of laser surface contour scanning to determine surface structure as required for certain applications
3  Physical correlation of pixel data for precise reconstruction of the subject's anatomical structure
4  In situ validation
5  Establish protocol for image acquisition and transport
6  Troubleshooting of various imaging parameters - Size, intensity, orientation, spacing, etc.
7  Image file format, size, and transport medium
8  Image/subject database
9  Integrate with CAOS (computer assisted orthopedic surgery) system, as appropriate
10 Perform Image reconstruction
11 NURBS interpolation of boundary points
12 Contour based reconstruction for semi-parametric CAD modeling
13 Point-cloud reconstruction for explicit CAD modeling
14 Morphing for implant fitting/sizing/design revision
15 3D surface and solid modeling of internal features
16 Export to IGES/STL format for FEA and CAM
17 Cross-calibration across imaging/CAD/CAM systems
18 Data acquisition and reduction Image Calibration:

In some embodiments, a multimodality deformable phantom is constructed to calibrate and validate the imaging system's ability to precisely capture the physical dimension of a 3D object in various view areas. The phantom consists of sets of 3D markers with known physical dimension and locations. The fiducial markers (Region of Interest (ROI) S7 are identified on the image yielding their voxel coordinates which are used to calculate the marker distances and polygonal areas in comparison with the physical measurements obtained from a 3D laser surface scanner and digital calipers. Image calibration coefficients are estimated using a least square algorithm.

Furthermore, after 3D reconstruction of the phantom model from the images, axial calibration is conducted for calibrating the marker axial distance and volume in comparison with the physical measurements obtained from a 3D laser surface scanner and digital calipers. Imaging parameters are also calibrated to attain the minimum resolution of the imaging system. For accurate replication of the subject-specific anatomy further onsite calibration is done by simultaneously imaging a smaller scale phantom while the subject images are acquired. After the region of interest is identified, then the subject and other clinical personnel participate in discussion of the available therapeutic technique/intervention necessary (S8-S10). This is followed by a determination of the required surgical operations and specifications, S11. The data is then transferred to the radiologists and bio-imaging personnel, S12/S13.

Surface Reconstruction:

In some embodiments, a series of the calibrated images are then segmented (S14) and registered (S15). An image is segmented first by dividing it into different regions of homogeneous properties. Each anatomic component (class) is classified into separating surfaces as defined by discriminant functions. After a finite number of unstructured boundary points are computed (S16) in a slice through the segmentation process, curve fitting using cubic splines or non-uniform rational B-splines (NURBS) S17, is done with the boundary points to generate boundary curves (S17) of each anatomic component for further geometric reconstruction. Subsequently, for surface modeling and 3-D geometric reconstruction lofting operation is done with a series of the refitted boundary curves (BCs), S20. In addition once the image is displayed the image is validated, S19, using collaboration software. Following the display of the 3-D solid models, S20, the model is validated by the clinician, S21 and the displayed 3-D solid model is exported to the engineering personnel for final design of the device which includes finite element analysis and human motion simulation S23.

Clinical Evaluation:

In some embodiments, clinical evaluation is made to determine the desired morphology of areas to be resectioned and an initial determination is made of how an implant will be shaped to make the necessary repair. Additional clinical data may also be used in this determination, as appropriate based on the best possible medical practice. Multiple data sources for may be used for calculating a recommended resection profile. In some embodiments, CAD is used to determine the geometric variance between the healthy bone and the diseased bone. In some embodiments, MRI pixel data is used to determine the manifestation of diseased; or damaged bone through comparing the healthy bone pixel density to the symmetrical damaged or unhealthy bone (e.g. cancerous or broken). In some embodiments, curves from multiple data sets are merged into a single three dimensional non uniform rational b-spline (NURBS). The surgeon, through the haptics graphical user interface is able to offset the recommended resection profile (RRP) by a constant or variable offset of the RRP based on his/her discretion. In some embodiments, additional clinical information includes subject history for relevant parameters including a complete medical history with emphasis on factors that alter strength of tissues such as general health, anthropometric measures such as height and weight, activity, skeletal and connective tissue health factor including bone density, and others that are critical for application. (FIGS. 2, 3A-3D).

In some embodiments, the transfer of information to and from surgeon (S21-S23) is ideally performed with a virtual 3D digital model of subject data that is calibrated for image spatial/spectral resolution and processed to accurately replicate the physical dimensions of the subject-specific anatomical structures. This dataset is transmitted electronically to the clinician who is able to manipulate the digital model dynamically in order to view any necessary aspect of the structure. Using collaboration software such as for example, Microsoft® Office 365-Lync (Microsoft, Redmond, Wash.) the surgeon then marks the area for any necessary clinical manipulation such as excision, and labels additional areas such as desirable locations for attachment of the prosthetic, regions that must be left alone, and provides other annotations regarding the surgical procedure and factors that should be addressed in the design of the final implant. This data is then communicated, digitally in some embodiments, back to the manufacturing firm, S24, where further evaluation and design is performed. In cases where surgeons are not comfortable with virtual 3D digital model, or where such computational and visualization hardware is not available, the surgeon can receive a dimensionally calibrated physical replica of the 3D digital model (S20-22) of a polymer or other material that is then manually marked by the surgeon (S21).

Implant Design Based on Clinical Evaluation:

In some embodiments, the desired shape of the implant is evaluated with respect to the intended surgical procedure based upon multiple factors. These include biomechanical Finite Element Analysis (FEA) of tissue and FEA of implant material, S25, mechanisms for short-term and long-term tissue bonding and attachment, desired surgical procedure, material choices, and the incorporation of any pre-engineered standard elements in the implant, S26. Finite Element Analysis is well known in the art and is a computer simulation technique in which the object is represented by a geometrically similar model consisting of multiple, linked, simplified representations of discrete regions or finite elements on an unstructured grid. See, for example, *Finite Element Methods for Structures With Large Stochastic Variations*, Elishakoff, 1. and Ren, Y, 2003; *Finite Element Methods With B-Splines*, Hollig, K., 2003. Standard elements may include articulation components (such as the ball and socket of a prosthetic hip joint), joinery to enable multiple sections of an implant to be assembled and attached during the surgical procedure, and design features to enable the device to be adjusted in size or shape during the initial implantation and at a future time post implantation; if desired. FEA provides a mathematical method to solve the limitations of the implant based on the geometric design and material type used, S27.

In some embodiments, the general fit of the device is designed based on the shape of the tissue it will interact with, as primarily determined from the CT, MRI, PET, X-ray, ultrasound, and related calibrated medical imaging data. In addition, for some tissues such as maxillary, facial and skull reconstruction where external appearance is critical, quantitative external imaging and shape scanning are used to obtain good esthetics using 3-D laser surface scanners (FIG. 4), S27.

In some embodiments, materials used in the device are chosen for biocompatibility such as metal alloys commonly used in medical devices including CoCrMo, Titanium alloys and commercially pure Ti (cpTi), medical grade stainless steels, tantalum and tantalum alloys, and others including included ceramics and oxides that can be incorporated into the design. The regions that will adhere to bone, when desirable, may be formed of cpTi to enhance bone attachment, and/or incorporate specific 3-D textures, modulus, other materials (such as oxides, minerals, glasses) or incorporate other properties to promote bone attachment and ingrowth that are known in the art.

In some embodiments, the material and device-bone material interface can be different in different locations, such as to provide different interfaces with cortical and cancellous bone to alter attachment and local biomechanical interaction. Finite element analysis mechanical simulations of tissues and the implant (S24-S30) are used to optimize the interaction to provide best possible function and minimize stress shielding. In addition to variations of the prosthetic material and the material thickness, internal material structures such as honeycombs, struts or ribs may be designed in to tailor the local and the global biomechanics of the device. Table 2 outlines the methodology for FEA simulation.

TABLE 2

| | |
|---|---|
| 1 | FE model generation |
| 2 | Pre and post-operative conditions |
| 3 | Optimum selection of element type and size |
| 4 | Mesh optimization for convergence |
| 5 | Material properties |
| 6 | Image based assessment |
| 7 | Noninvasive onsite testing |
| 8 | Solution |
| 9 | Linear vs. nonlinear |
| 10 | Functional assessment and validation |

Figure 5:
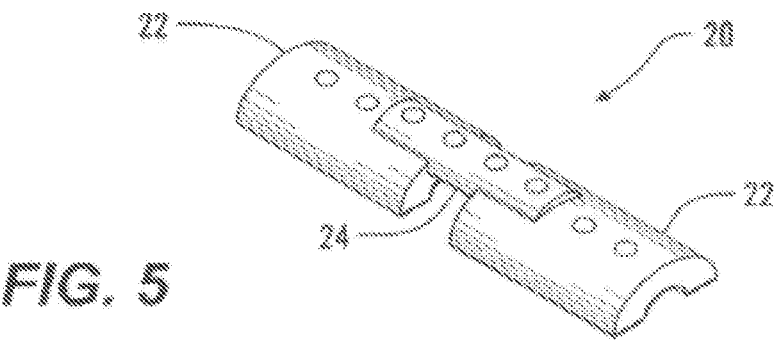
FIG. 5 illustrates an embodiment of the present invention for providing an adjustable plate prosthetic for surgical repair. In this embodiment, the plate has two similar anchor ends that are adjustably connected using a slidable and fixable bridge.
Figure 6:
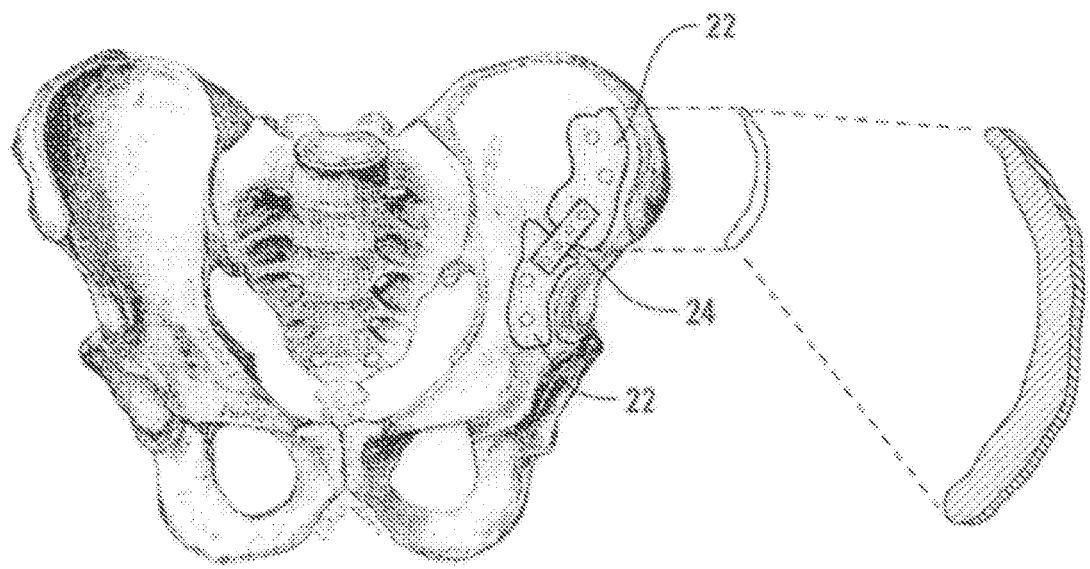
FIG. 6 illustrates an embodiment of the present invention wherein the invention provides an adjustable multiple plate prosthetic for surgical repair of the ilium.
Figure 7:
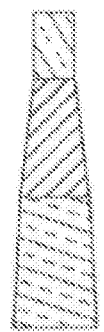
FIG. 7 illustrates an embodiment of the present invention wherein the invention provides a complex stent with multiple segments and multiple elements in each section.

In some embodiments, as required for an application, the implant may be designed in multiple components. For example, it is clinically desirable to bridge or surround ligament attachments that are otherwise healthy for reconstruction of a diseased or traumatized pelvis. Separate, attachable, components of the implant are then designed to surround such structures, and the components are then assembled and attached as necessary in surgery. FIG. 5 represents an implant 20 having opposing anchor ends 22 that are adjustably connected using a sliding bridge 24. In use, such an implant may be used to reconstruct the traumatized pelvis FIG. 6. In some embodiments, the two anchor ends are produced according to the data obtained using MRI and CAT images as discussed above and shown in FIG. 3A-D. The anchor ends 22 are put in place, spanning the damaged area and the bridge 24 holds the anchors ends 22 together. Further, it should be appreciated that using the methods described herein, the anchor ends (or any other part of the device) may be constructed with variable thickness and shape to best fit the pelvic tissue and provide the appropriate biomechanical properties.

In some embodiments, the design of the implant will allow onsite adjustments, where feasible and desirable, since even the best solid model will not always be a perfect representation of the tissue exposed during surgery. This will enable the surgeon to make necessary adjustments during the procedure.

In part this may be due to the imperfect tools and especially relatively coarse method of hand-held burrs and other tools used to remove bone during surgery. As required, specific tools and guides can also be designed and produced to assist tissue preparation.

In some embodiments, the ideal method to attach an orthopedic prosthesis is determined through anatomic and biomechanical evaluation of the healthy bone. Analysis will determine the best locations, best orientation angles with respect to loading, and related biomechanical analyses. Conventional bone-screw technology may be used by the surgeon to make this attachment. Multiple locations for bone-screws will enable the surgeon to determine the optimum choices during the procedure to ensure attachment to high strength bone. As needed, a biomechanical analysis of alternate screw locations may be provided to the surgeon. Flanges and wings may be used to support less strong areas with thin cortical bones and/or remarkable trabecular bones, while flanges on both sides of a structure with a thru connection can provide solid anchoring when required. Fitting the device in place may be accomplished with plates that bridge prosthesis with remaining tissue. Such plates can be provided in several sizes when adjustability may not be possible or provide sufficient range.

In some embodiments, as required for a specific application, the prosthetic may be designed with intrinsic adjustability to alter the fit during surgery using features such as sliding joints (e.g. sliding dovetails) or overlapping plates (FIGS. 5 and 6), S28. Such features may also be used to alter fit post surgery if required due to growth or other factors or needs. Such an adjustable fixture includes an internal Ilizarov device to enable the expansion or lengthening of long bones. Access to the adjusting structure is designed so that such alterations are made with minimal surgical trauma, such as minimally invasively.

Evaluation of Designed Implant by Clinician:

In some embodiments, the implant design is evaluated by the clinician, S29, using virtual 3-D presentation methods and/or solid models as illustrated in FIGS. 3A-3D and 4A-4D. Fit is checked, methods of attachment to healthy tissues are evaluated, methods of assembly of implant components (if multiple components are evaluated, and the entire surgical procedure is performed "virtually" using 3-D display and related methods and/or with solid models. If required, steps 3 and 4 shown in TABLE 2 and steps S25-S29 (FIG. 2B) are repeated until a final digital design and surgical plan are made, S30.

In some embodiments, the final design of the implant is created digitally using CAD solid modeling to precisely match the factors determined above, S31. This includes the overall shape, choice of material or materials, thickness and thickness gradients at all locations, design of internal structures such as honeycombs to provide ideal modulus, placement of pre-engineered standard elements, surface materials (if different from bulk), surface texture, and any other necessary features. The spatial resolution of the design is ~10 um to correspond with the manufacturing resolution and material handling capabilities of the direct manufacturing tooling and processes.

In some embodiments, pre- and post-operative clinical and biomechanical assessments are made for functional assessment of the custom implants. Clinical evaluations include joint range of motion and strength testing. For biomechanical assessment finite element analysis simulations are used to develop models with the implant in-situ. Various loading conditions are tested to predict stress localization in the interface and stress shielding. Model parameters are obtained from the image data and material testing of biopsy specimens harvested during surgery, S30.

In some embodiments, pre- and post-operative clinical and biomechanical assessments are made for functional assessment of the custom implants. Clinical evaluations include joint range of motion and strength testing. For biomechanical assessment finite element analysis simulations are used to develop geometric CAD solid models with the implant in-situ through virtual surgical operation simulating the actual surgery done to the subject. A number of 10 noded 3D tetrahedral elements are used to create finite element meshes of the geometric models. Mesh convergence analysis is conducted for accurate simulations. Various loading conditions as obtained from the literature and pre- and post-operative functional testing of the subject are tested to predict stress localization in the interface and stress shielding. Model parameters are obtained from the image data and material testing of biopsy specimens harvested during surgery. A linear static analysis is conducted to obtain first-order solutions. As needed, more sophisticated analysis such as nonlinear and transient analyses are conducted to reflect the level of physical activities of the subject. The simulation results are cross-validated with those from the pre- and post-operative functional testing and further biomechanical assessments are done accordingly.

Example II

Production

First Embodiment

In some embodiments, the design created above is produced using direct computer aided manufacturing (CAM) digital methods to produce the implant with laser-based additive free-form manufacturing as described above, S33. In some embodiments, production of each component is performed with the desired material or materials directly from powdered metals (and certain other materials) that are delivered to the desired spatial location and then laser annealed in place (using, for example, DMD, LENS or the like) or annealed using an electron beam (EBM). This produces a very high strength fine-grain structure, enables the production of internal features, enables layers of multiple materials, gradients of material properties, inclusion of ancillary internal elements, and produces resultant structures that generally require minimal post-production processing.

In some embodiments, multiple materials are applied sequentially, locally, and in specific locations, if required to achieve desired properties For example, the bone interface aspect of a bulk Ti6 implant can be produced with cpTi to enhance bone bonding, or a gradient of materials may be created to affect galvanic processes.

In some embodiments, Nitinol (NiTi) shape-memory alloy structures are entirely Ti on the surface to minimize Ni toxicity.

In some embodiments, and as desired during the additive manufacturing approach, the process is stopped and an element added, followed by continued additive manufacturing. Such elements can include functional sensors such as MEMS devices including, but not limited to, neuronal, neuromuscular or skeletal stimulators, optical elements such as lens, structural elements such as ceramic whiskers, or other elements to provide functional or other capabilities. Any material or device can be incorporated that is not damaged by the thermal, optical and other constraints posed by the laser or electron additive manufacturing process, and in consideration of the laser or electron additive manufacturing process resolution limits.

Example III

Post Production

First Embodiment

In some embodiments, necessary post production processes are performed on the implant. In some embodiments, post production processes include subtractive manufacturing processes for finish machining operations, grinding and polishing as may be required for joining surfaces and for bearing surfaces, such as in articulation joints, etc. Additional processing such as ion beam implantation or annealing may also be performed may be performed. The surface texture resolution of the additive manufacturing process is currently ~10/μm with no rough or abrupt transitions. It is thus intrinsically suitable for many tissue interfaces without further processing. For example, this texture limit can enable the direct production of tissue interfaces with features that may be as small as 10/μm, or larger features as desired in order to enhance tissue interactions such as bone growth into the implant. Other post production processes include ion beam implantation, as is routinely used to harden bearing surfaces in prosthetic knees and hips, as well as annealing and other thermal treatments to affect material structure.

Preparation for Transport and Clinical Use

After the production processes the device is then cleaned, sterilized, packed, labeled, and shipped as necessary for the actual surgical application, S34/S35 where the process ends.

Example IV

Applications of Technology

In some embodiments, using the methods and technology described above, personalized implantable devices may be created for a wide variety of clinical implants including skeletal orthopedic appliances for repair of long bones (including plates, intramedullary rods and total joint prosthetics or portions thereof), pelvic reconstruction appliances, appliances for repair of cranial defects or damage, maxillofacial repairs, dental prosthetics, and cosmetic enhancements, others that will be apparent to those skilled in the art.

In some embodiments, a unique feature of this invention is designed-in intrinsic adjustability to alter the fit during surgery using features such as sliding joints (e.g. sliding external or internal dovetails) or overlapping plates (FIGS. 5-8). Such features may also be used to alter fit post-surgically if required due to growth or for therapeutic reasons such as with an internal Ilizarin device. Access to the adjusting structure can be planned so that such alterations can be made with minimal surgical trauma, such as minimally invasively or even without invasion using an implanted actuator controlled remotely by an external signal (such as radio frequency control), or directly by percutaneous transmission (such as via momentarily or long term inserted control lines).

In some embodiments, the methods described above may also be used for the design and development of personalized devices for external fixation, such as used for aligning long bones and the spine, and for generic or non-personalized devices intended for external or implanted orthopedic intervention, and others that will be apparent to those skilled in the art.

In some embodiments, the unique capabilities of the design and manufacturing process enable multiple elements to be incorporated in monolithic structures, internal features of virtually any desired geometry, and the creation of shapes that are not readily created with other methods; such as complex curves and sliding joints.

In some embodiments, an application of a complex device is a curved external fixture for an Ilizarov device. Other applications include supporting fixtures for neck or spine trauma that accurately fit the subject, and personalized casts and articulation brace devices with adjustability so that range of mobility can be slowly introduced as required for physical therapy.

In some embodiments, the methods described above may also be used for the design and development of personalized and generic devices for implanted non-orthopedic applications such as for cardiovascular, neurological, digestive or other interventional implants used for soft or hard tissue repair. The method allows superior devices to be made, such as, for example, geometrically complex stents (FIG. 7) due to the unique capabilities of the design and production invention described above, including, but not limited to produce devices having varying alloy content, the ability to include honeycombs-shaped internal structures, hollow internal structures, full or partial rib internal structures, struts, wings and other complex features not possible using conventional subtractive machining technology, such as for example, functional elements such as sensors, actuators, stimulators and the like, and for other applications that will be apparent to those skilled in the art.

In some embodiments, the unique capabilities of the design and manufacturing process enable multiple elements to be incorporated in monolithic structures, internal features of virtually any desired geometry, and the creation of shapes that are not readily created with other methods. Examples include stents of any shape, with spatially variable material flexibility, and expendability. Other examples include staples, clips, pins and other devices to effect tissue closure or positioning, cases for devices such as pacemakers and other encapsulated electronics, sensors, and actuators, dimensionally complex multiple material (as required) detection and stimulation electrodes, neuro-stimulators and sensors, and valve prosthetics, and components such as stents (frames) used in tissue valves.

In some embodiments, the methods described above may also be used for the design and development of interventional tools and instruments such as required for laparoscopic, interventional radiological and minimally invasive procedures for cardiovascular, neurological, digestive or other applications in soft or hard tissue. Using this invention, superior devices may be made such as geometrically complex cardiovascular, urological and biliary stents (FIG. 7) due to the unique capabilities of the design and production capabilities of this invention. Moreover, the design capabilities for fitting structure and biomechanics to achieve optimal devices can also be applied to the physician using these devices in order to create medical and other tools that will be more comfortable and thus provide superior performance by anatomic and biomechanical fitting of the device to the user and to the necessary motion used for the procedure.

Figure 8C:
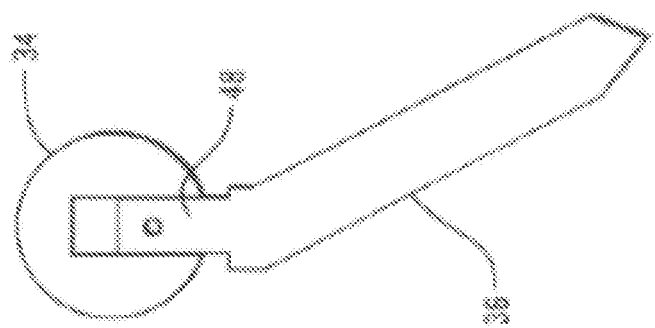
FIGS. 8A-8C illustrate particular features of an artificial hip.
Figure 8B:
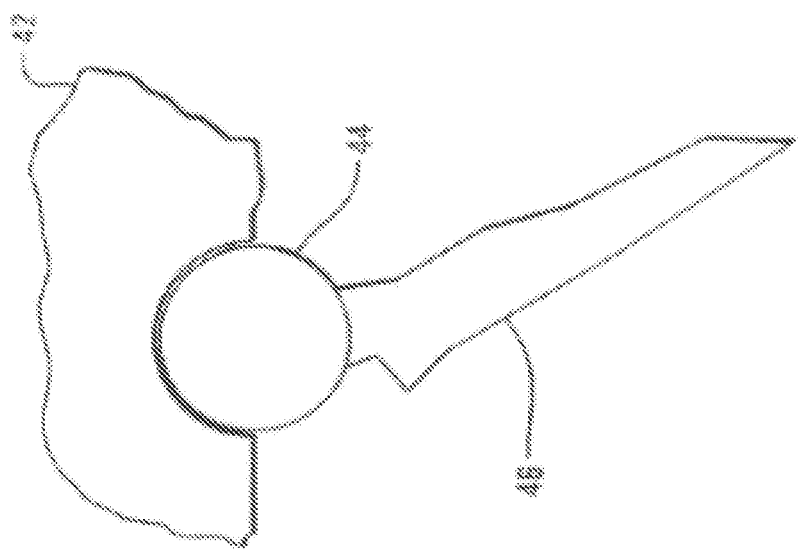
Figure 8A:
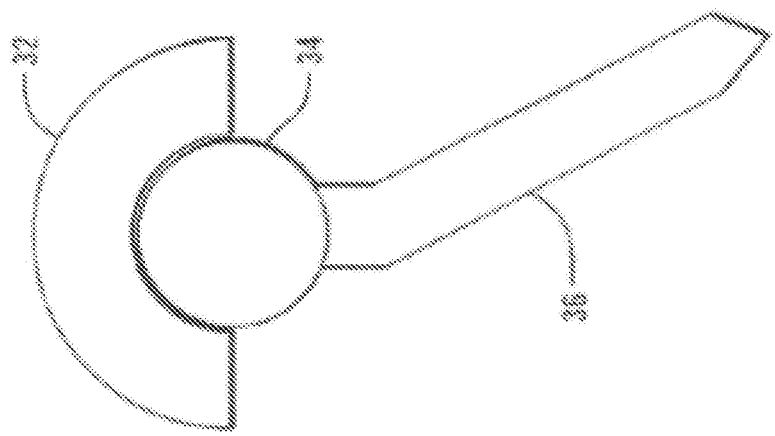

In some embodiments, the invention can be used to create hybrid prosthetic devices such as, for example, artificial hips. In some embodiments, illustrated in FIGS. 8A-C, the invention can be used to create a prosthesis that is designed to fit into the subjects existing skeletal architecture. FIG. 8A illustrates a conventional prosthetic hip including acetabular cup 32 and integral ball 34 and stem 36. FIG. 8B illustrates a personalized prosthetic hip with acetabular cup 42 shaped to fit subject contours (as required due to disease, trauma, etc.), with standard integral ball 44 and stem 46, with the stem 46 designed as described and illustrated in FIG. 3 to precisely fit the subject's intramedullary space, femur contours, and have a specific texture and/or material to improve bone interface. FIG. 8C illustrates conventional prosthetic hip ball 34 and stem 36 with adjustable bridge 48 between (otherwise conventional) ball and stem. In this example, the fastening device, such as, a pin or screw to lock position is not shown.

In some embodiments, the unique capabilities of the design and manufacturing process enable multiple elements to be incorporated in monolithic structures, internal features of virtually any desired geometry, and the creation of shapes that are not readily created with other methods. This includes (1) curved tubes with telescoping elements and multiple lumens; (2) stents and other devices that do not require laser cutting with consequent production of sharp edges; (3) shapes that are not readily produced with conventional machinery including wall thicknesses, bifurcations, element spacing, inside and outside diameters, and extensibility that vary along length; and (4) materials that include composites of multiple metals.

It is recognized that modifications may be made by one of skill in the art of the invention without departing from the spirit or intent of the invention and, therefore, the invention is to be taken as including all reasonable equivalents to the subject matter of the appended claims.

Example V

Onboard New Facility and Clinicians

Second Embodiment

Figure 9:
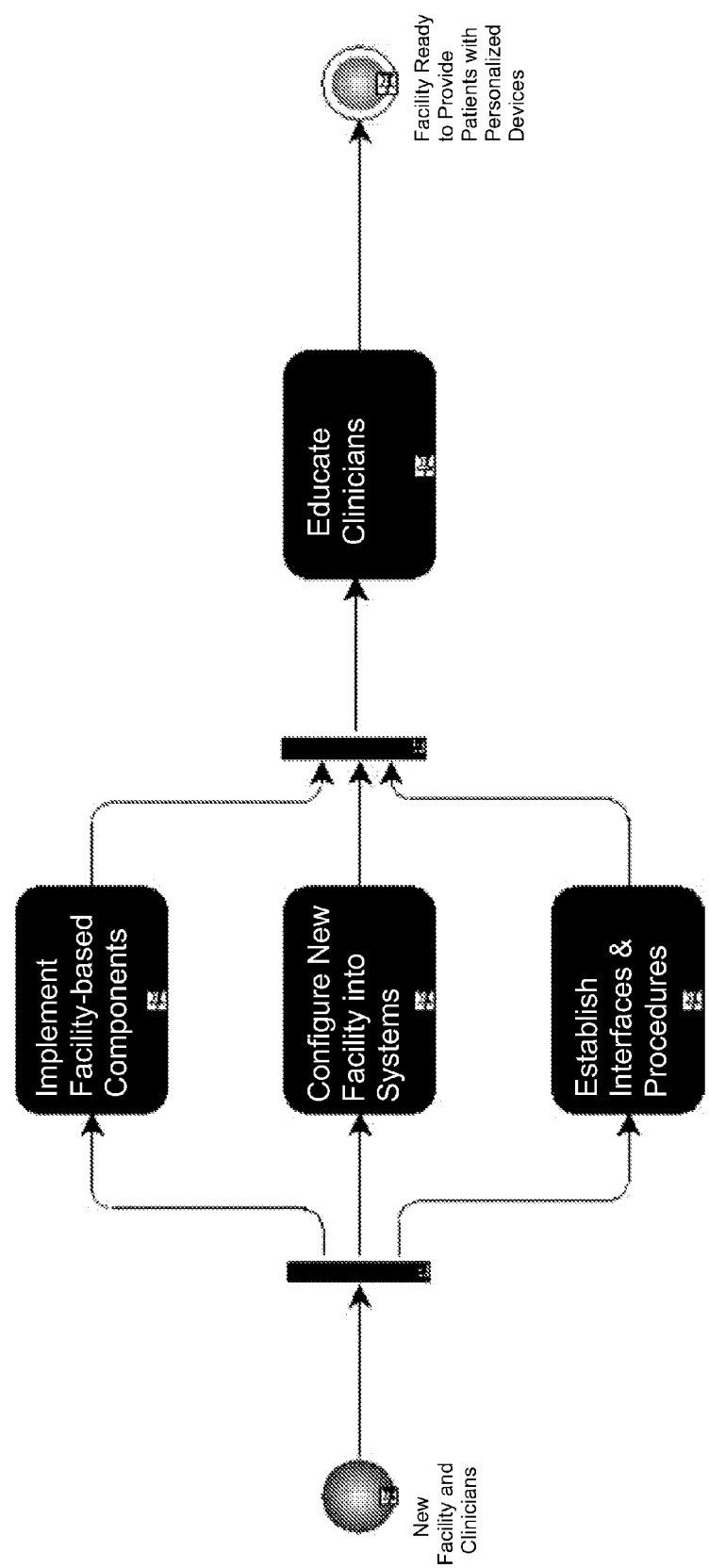
FIG. 9 illustrates a schematic of one embodiment of the present invention depicting general methodology used for preparing a facility and its' clinicians and/or practitioners to be able to use the systems and devices described in this invention (Second Embodiment of invention).

In some embodiments, using the methods and technology described herein and based on FIG. 9, a facility and/or the practitioners therein, will need to be Onboarded. That is to say that they need to be knowledgeable in and be prepared to provide the methods, devices, systems, and instruments related to medical implants and surgical instruments produced for personalized fit and/or personalized function of individual users.

In some embodiments, facility-based components including instruments and technology will need to be implemented. The new facility and the practitioners will need to be configured into various automated systems.

In some embodiments, various technical and procedural interfaces between facility and the company need to be established.

In some embodiments, in the beginning and repeated as necessary, orthopedic surgeons and other clinicians and technicians are educated as follows:

learn how to engage the herein described process gain knowledge in the advantages of personalized fit and/or function gain knowledge in the various technologies and applications used within the herein described process learn collaboration approach to design experience intuitive and easy-to-use graphical user interface understand haptics (computer simulation of the sense of touch) device Example VI Provide Patient with Personalized Device Second Embodiment The driving principles behind the processes and methods are to utilize a collaborative approach that includes the expertise of the surgeon in the design, incorporate advanced manufacturing technology for mass-production (adaptive machining) and implant validation, and produce cost-effective, patient-specific implants in 48 hours or less.

Figure 10A:
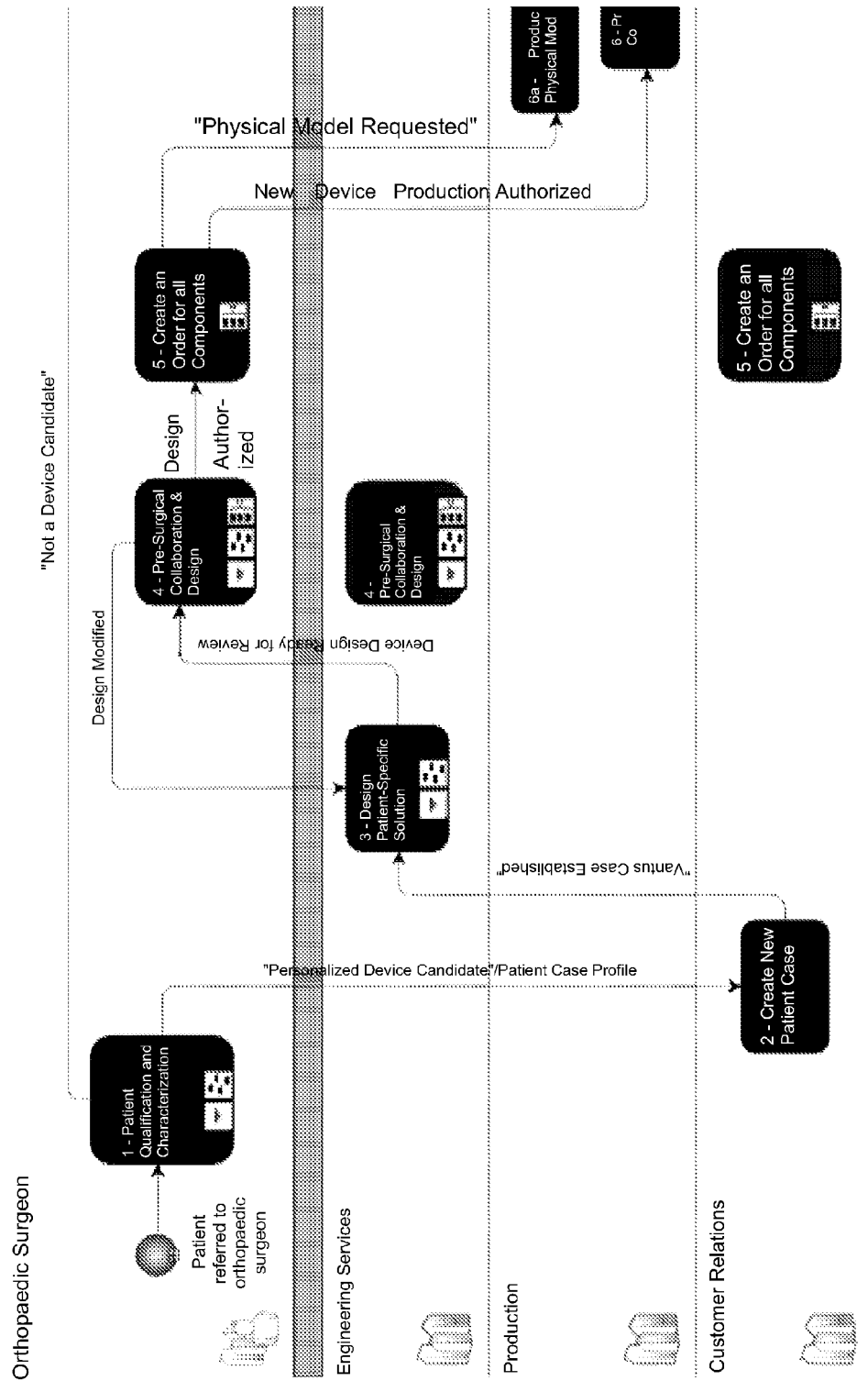
FIGS. 10A and 10B illustrate a schematic of one embodiment of the present invention depicting general methodology used for creating personalized medical implants and prosthesis described in this invention (Second Embodiment of invention).
Figure 10:
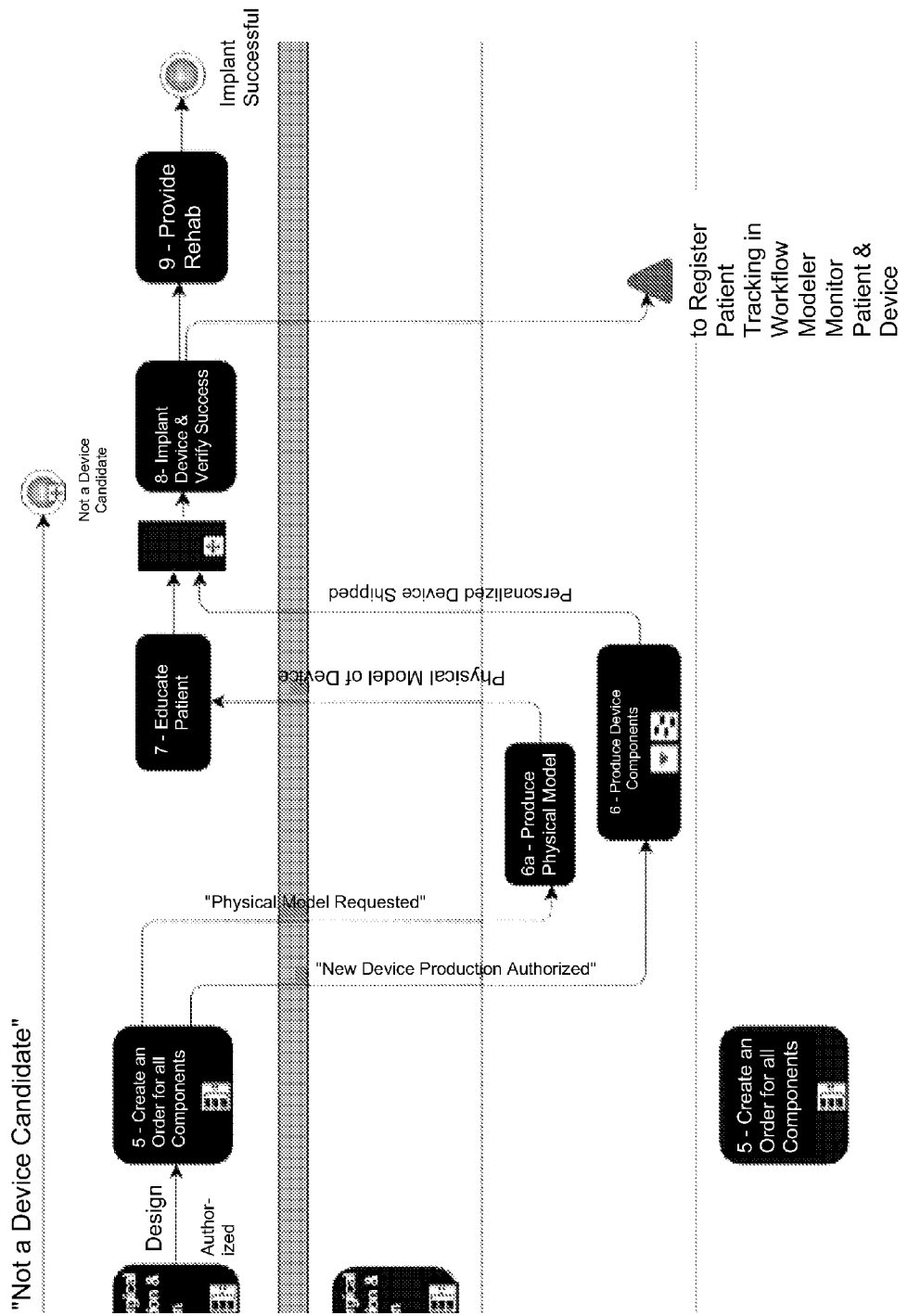

In some embodiments, using the methods and technology described herein, and based on FIGS. 10A and 10B, the process begins with the presentation of orthopedic-related pain to an Orthopedic Surgeon and ends with the rehabilitation following implant surgery. The surgeon qualifies the patient and collects data and images which are sent to the manufacturing firm where a new case is created. A patient-specific solution is designed and then presented to the surgeon for pre-surgical collaboration.

In some embodiments, following design authorization, an order for all Device Components and an optional physical model is created. The term Device has referred to the primary device to be implanted (e.g., hip, knee) but typically includes the collection of all Device Components. A Component could be the Device (e.g., trauma plate), or a part of a Device (e.g., ball and socket), or a surgical tool (e.g., Cutting Tool) or other part (e.g., Screw) used to implant the Device. Upon authorization of the Device Design, an order for the production and/or acquisition of all Device Components that are required for this particular patient (and surgeon) is created. The entire Order is managed through the entire Production process.

In some embodiments, per the Patient Order, all required components are produced and/or acquired and the entire order is shipped, in some embodiments, within 48 hours of the Order being placed. Device implantation takes place, success is verified and rehabilitation is provided.

Example VII

Patient Qualification and Characterization

Second Embodiment

Figure 11:
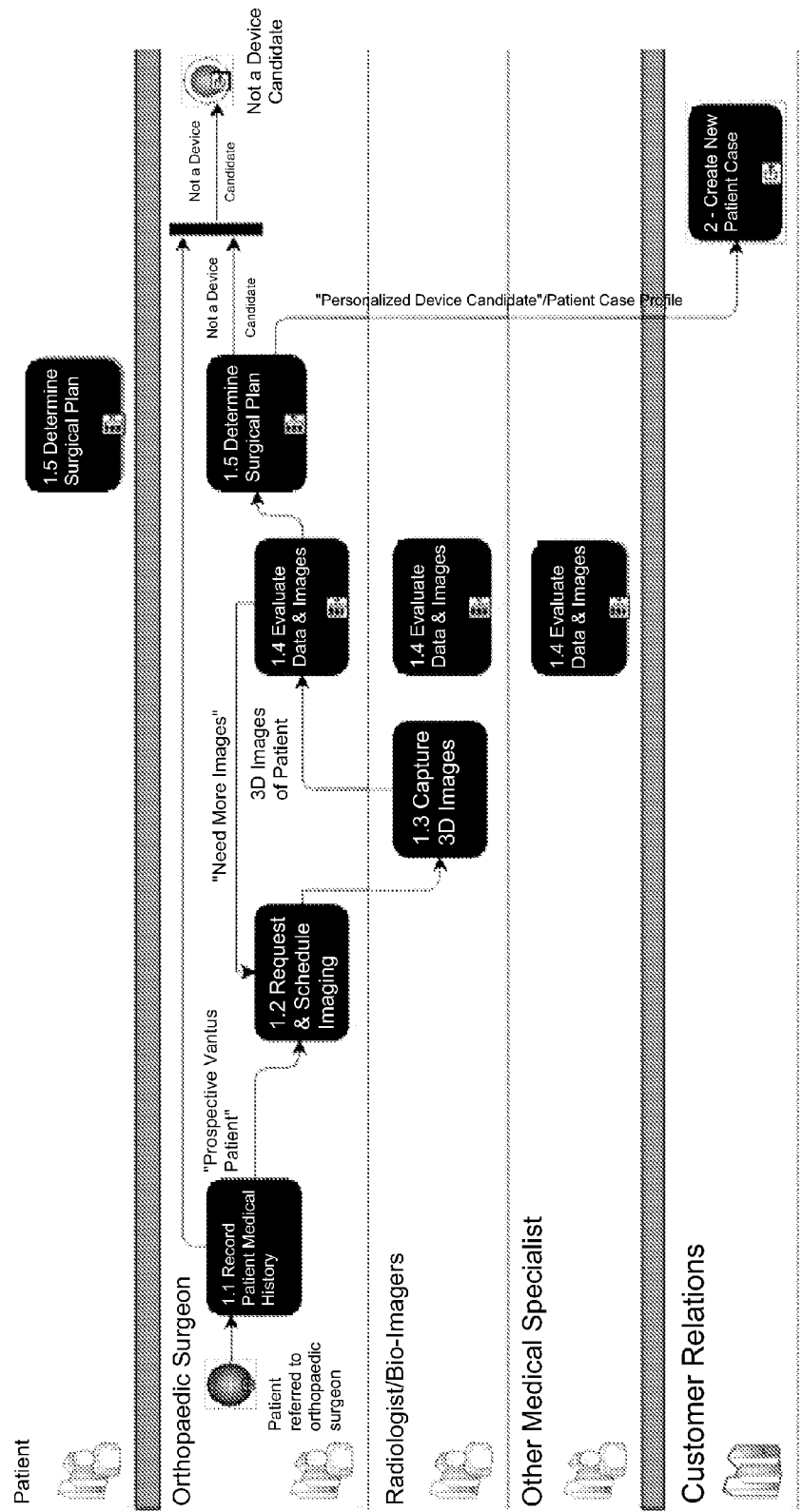
FIG. 11 illustrates a detailed schematic of one method of patient qualification according to some embodiments as illustrated in FIG. 10 (Second Embodiment of invention).

In some embodiments, using the methods and technology described herein and based on FIG. 11, a patient is qualified as an appropriate candidate for a personalized implant.

Record Patient Medical History, 1.1: In some embodiments, the subject's physical data, genomic data and medical history information are recorded, including medical imaging data, age, genetic disease predisposition, allergies, potential exposure to bacteria strains (soldiers in Iraq and Afghanistan), and pre-treatment activity level.

Request & Schedule Imaging, 1.2: In some embodiments, some images require advanced scheduling. The clinician must request specifics for what is to be imaged and determine the type of 3D imaging (CT, MRI, PET, digital X-ray, ultrasound, and others). The clinician should establish imaging parameters like size, intensity, orientation, spacing, etc. and identify the region of interest for imaging.

Capture 3D Images, 1.3: In some embodiments, three-dimensional image data is obtained from the subject. The image is calibrated for engineering use during design.

In some embodiments, a multimodality deformable phantom is used to calibrate and validate the imaging system's ability to precisely capture the physical dimension of a 3D object in various view areas. The phantom comprises sets of 3D markers with known physical dimension and locations. The fiducial markers (Region of Interest (ROI)) are identified on the image yielding their voxel coordinates which are used to calculate the marker distances and polygonal areas in comparison with the physical measurements obtained from a 3D laser surface scanner and digital calipers. Image calibration coefficients are estimated using a least square algorithm. Furthermore, after 3D reconstruction of the phantom model from the images, axial calibration is conducted for calibrating the marker axial distance and volume in comparison with the physical measurements obtained from a 3D laser surface scanner and digital calipers. Imaging parameters are also calibrated to attain the minimum resolution of the imaging system. For accurate replication of the subject-specific anatomy further onsite calibration will be done by simultaneously imaging a smaller scale phantom while the subject images are acquired.

Evaluate data and images, 1.4: In some embodiments, three-dimensional image data is presented for clinical evaluation with the cooperation of multiple specialists. After the medical imaging is evaluated, the subject and other clinical personnel participate in discussion of the available therapeutic technique/intervention necessary.

Determine Surgical Plan, 1.5: In some embodiments, a determination of the required surgical operations and specifications is made. If the patient is a candidate for a personalized device from the firm, then the Patient Case Profile data and images ("Case Material") are then prepared and transferred to the firm.

Example VIII

Design Patient-Specific Device

Second Embodiment

Figure 12A:
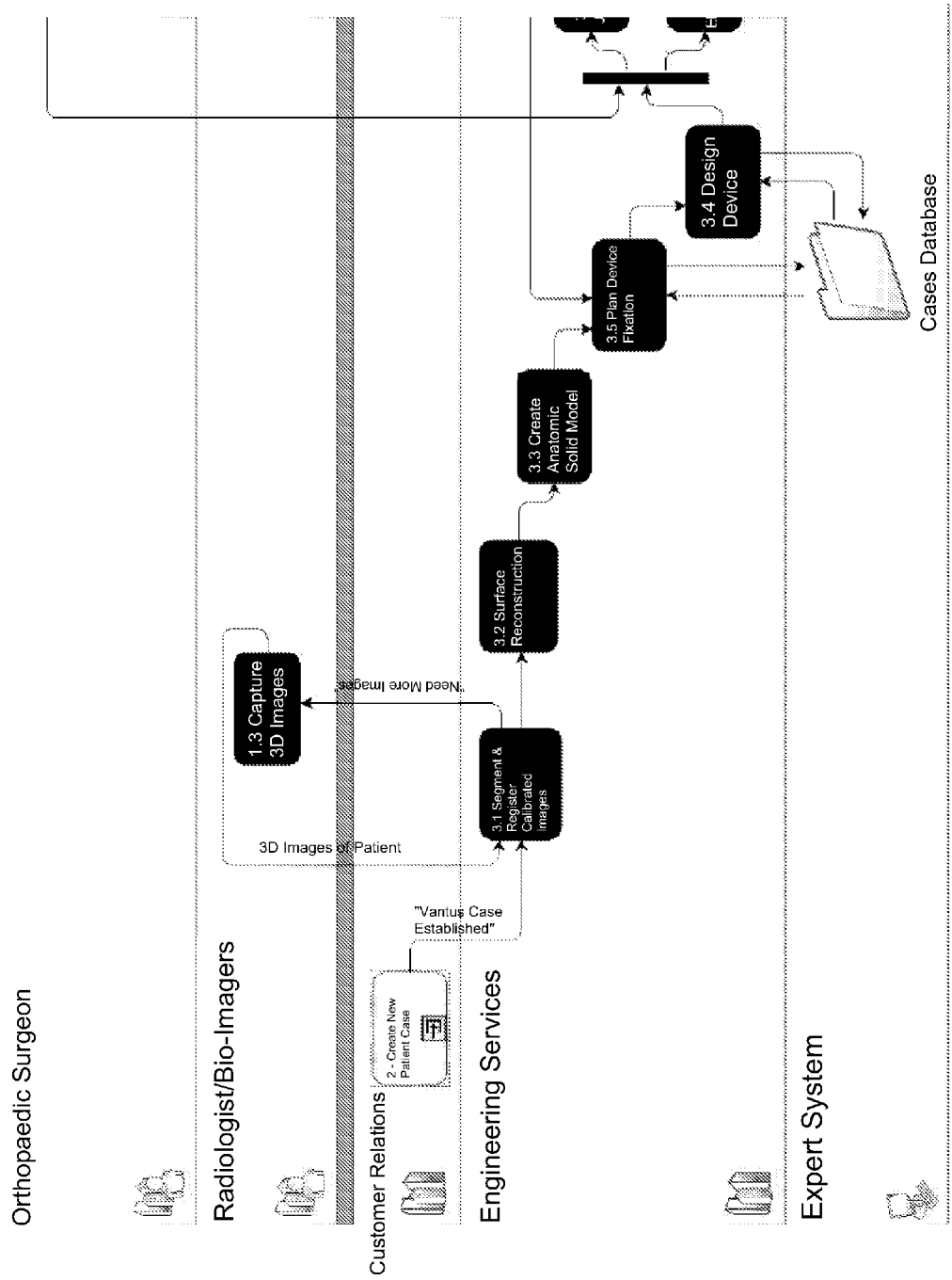
FIGS. 12A and 12B illustrate a detailed schematic of one method of device design according to some embodiments as illustrated in FIG. 10 (Second Embodiment of invention).
Figure 12B:
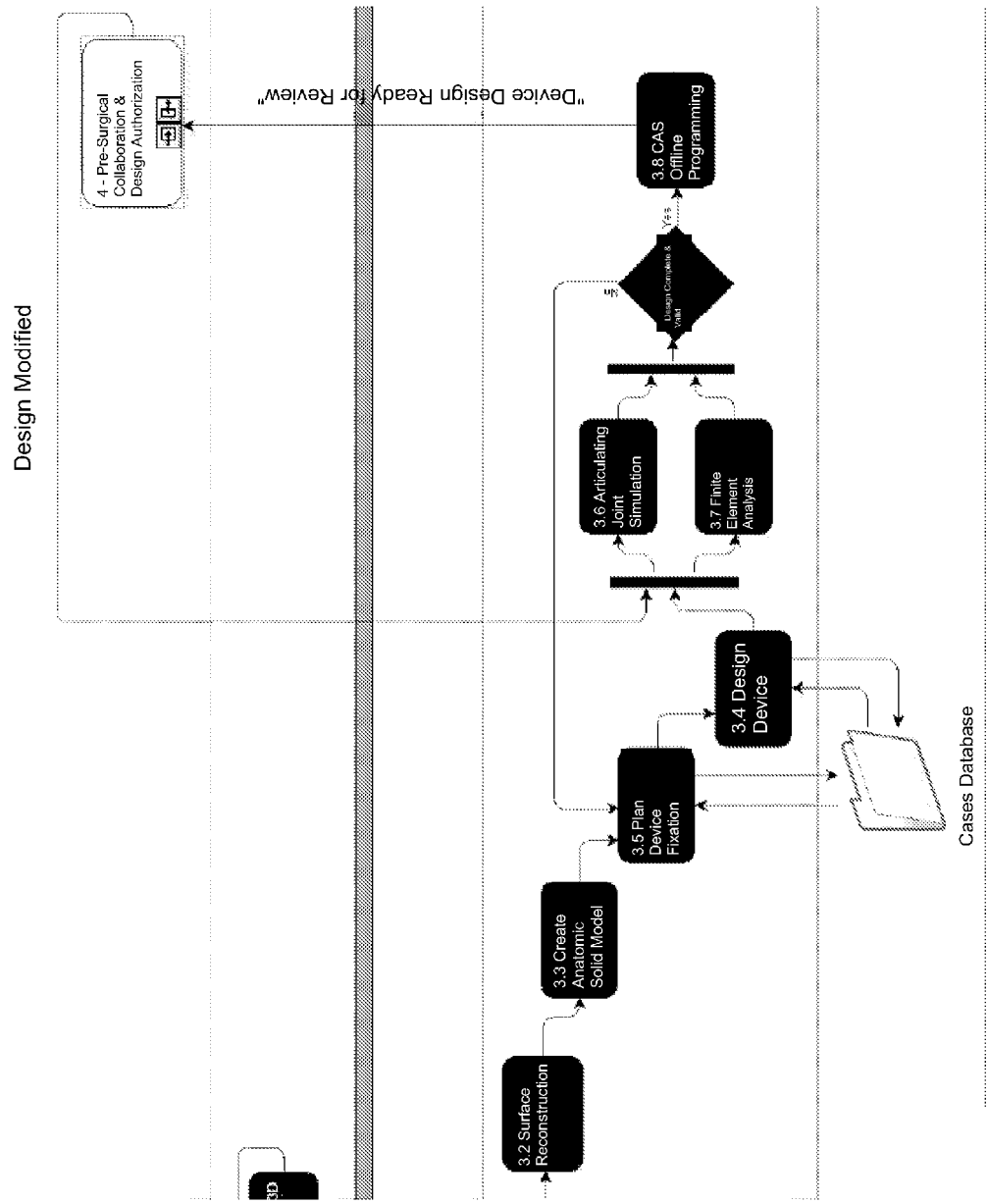

In some embodiments, using the methods and technology described herein and based on FIGS. 12A and 12B, a patient-specific solution is designed.

Segment and Register Calibrated Images, 3.1: In some embodiments, imaging data is verified, confirming acquired full region of interest, correct location, and correct size. A series of the calibrated images are then segmented and registered. Segmenting data identify relevant anatomical features. An image is segmented first by dividing it into different regions. A finite number of unstructured boundary points are computed in a slice through the segmentation process. Each anatomic component (class) is then classified into separating surfaces.

Surface Reconstruction, 3.2: In some embodiments, after a finite number of unstructured boundary points are computed in a slice through the segmentation process, a surface is created.

Create Anatomic Solid Model, 3.3: In some embodiments, an 'unintelligent' or non-parametric model is created from CT and MRI data. A parametric model is then created from the non-parametric model. Curve fitting is performed to create solid models. This may include using cubic splines or NURBS with the boundary points to generate boundary curves of each anatomic component for further geometric reconstruction. Subsequently, for surface modeling and 3D geometric reconstruction lofting operation is done with a series of the refitted boundary curves.

Plan Device Fixation, 3.4: In some embodiments, an engineer decides how the device will be attached to the bone (e.g., the degree of press fit) based on quality of preserved bone, patient profile variables and case-based reasoning intelligence. The regions that will adhere to bone, when desirable, may be formed of cpTi to enhance bone attachment, and/or incorporate specific 3D textures, modulus, other materials (such as oxides, minerals, glasses) or incorporate other properties to promote bone attachment and ingrowth that are known in the art.

In some embodiments, the general fit of the device is designed based on the shape of the tissue it will interact with, as primarily determined from the CT. MRI, PET, digital X-ray, ultrasound, and related calibrated medical imaging data. In addition, for some tissues such as maxillary, facial and skull reconstruction where external appearance is critical, quantitative external imaging and shape scanning are used to obtain good esthetics using 3D laser surface scanners (FIG. 4). In some embodiments, multiple data sources may be used for calculating a recommended resection profile (RRP). In some embodiments, CAD is used to determine the geometric variance between the healthy bone and the diseased bone. In some embodiments, CT voxel data is used to determine the manifestation of diseased or damaged bone through comparing the healthy bone voxel density to the symmetrical damaged or unhealthy bone (e.g. cancerous or broken). In some embodiments, curves from multiple data sets are merged into a single 3D NURBS. Robotic surgery is simulated for the resection profile.

In some embodiments, the ideal method to attach an orthopedic prosthesis is determined through anatomic and biomechanical evaluation of the healthy bone. Analysis determines the best locations, best orientation angles with respect to loading, and related biomechanical analyses. Conventional bone-screw technology may be used by the surgeon to make this attachment. Multiple locations for bone-screws will enable the surgeon to determine the optimum choices during the procedure to ensure attachment to high strength bone. As needed, a biomechanical analysis of alternate screw locations is provided to the surgeon. Flanges and wings may be used to support less strong areas with thin cortical bones and/or remarkable trabecular bones, while flanges on both sides of a structure with a thru connection can provide solid anchoring when required. Fitting the device in place may be accomplished with plates that bridge prosthesis with remaining tissue. Such plates can be provided in several sizes when adjustability may not be possible or provide sufficient range.

Design Device, 3.5: In some embodiments, all components of the device and all surgical tools are designed. A parametric model (intelligent, virtual, solid model) is created and is dependent on an anatomic model and may take certain features from it.

In some embodiments, following the display of the 3D solid models an initial device is designed referencing the imaging software and the successes and failures of past devices based on the case-based reasoning system.

In some embodiments, multiple data sources are used for calculating a recommended resection profile (RRP). In some embodiments, CAD is used to determine the geometric variance between the healthy bone and the diseased bone. In some embodiments, CT voxel data is used to determine the manifestation of diseased or damaged bone through comparing the healthy bone voxel density to the symmetrical damaged or unhealthy bone (e.g. cancerous or broken). In some embodiments, curves from multiple data sets are merged into a single 3D NURBS.

In some embodiments, materials used in the device are chosen for biocompatibility such as metal alloys commonly used in medical devices including CoCrMo, Titanium alloys and cpTi, medical grade stainless steels, tantalum and tantalum alloys, and others including polymers, ceramics and oxides that can be incorporated into the design. The regions that will adhere to bone, when desirable, may be formed of cpTi to enhance bone attachment, and/or incorporate specific 3D textures, modulus, other materials (such as oxides, minerals, glasses) or incorporate other properties to promote bone attachment and ingrowth that are known in the art.

In some embodiments, the material and device-bone material interface is different in different locations, such as to provide different interfaces with cortical and cancellous bone to alter attachment and local biomechanical interaction. FEA mechanical simulations of tissues and the implant are used to optimize the interaction to provide best possible function and minimize stress shielding. In addition to variations of the prosthetic material and the material thickness, internal material structures such as honeycombs, struts or ribs may be designed in to tailor the local and the global biomechanics of the device.

In some embodiments, as required for an application, the implant is designed in multiple components. For example, it is clinically desirable to bridge or surround ligament attachments that are otherwise healthy for reconstruction of a diseased or traumatized pelvis. Separate, attachable, components of the implant are then designed to surround such structures, and the components are then assembled and attached as necessary in surgery. FIG. 5 represents an implant 20 having opposing anchor ends 22 that are adjustably connected using a sliding bridge 24. In use, such an implant may be used to reconstruct the traumatized pelvis FIG. 6. In some embodiments, the two anchor ends are produced according to the data obtained using MRI and CT images as discussed above and shown in FIG. 3A-D. The anchor ends 22 are put in place, spanning the damaged area and the bridge 24 holds the anchors ends 22 together. Further, it should be appreciated that using the methods described herein, the anchor ends (or any other part of the device) may be constructed with variable thickness and shape to best fit the pelvic tissue and provide the appropriate biomechanical properties.

In some embodiments, as required for a specific application, the prosthetic may be designed with intrinsic adjustability to alter the fit during surgery using features such as sliding joints (e.g. sliding dovetails) or overlapping plates (FIGS. 5 and 6), item 24. Such features may also be used to alter fit post-surgery if required due to growth or other factors or needs. Such an adjustable fixture includes an internal Ilizarov device to enable the expansion or lengthening of long bones. Access to the adjusting structure is designed so that such alterations are made with minimal surgical trauma, such as minimally invasively.

In some embodiments, the final design of the implant is created digitally using CAD solid modeling to precisely match the factors determined above. This includes the overall shape, choice of material or materials, thickness and thickness gradients at all locations, design of internal structures such as honeycombs to provide ideal modulus, placement of pre-engineered standard elements, surface materials (if different from bulk), surface texture, and any other necessary features. The spatial resolution of the design is ~10 μm to correspond with the manufacturing resolution and material handling capabilities of the direct manufacturing tooling and processes. In some embodiments, volume is added automatically for production so that a higher tolerance surface can be created from a precision grinding operation establishing the final designed shape.

In some embodiments, the general fit of the device is designed based on the shape of the tissue it will interact with, as primarily determined from the CT, MRI, PET, digital X-ray, ultrasound and related calibrated medical imaging data. In addition, for some tissues such as maxillary, facial and skull reconstruction where external appearance is critical, quantitative external imaging and shape scanning are used to obtain good esthetics using 3D laser surface scanners (FIG. 4).

Loopback:

In some embodiments, the desired shape of the implant is evaluated with respect to the intended surgical procedure based upon multiple factors. These include biomechanical FEA of tissue and FEA of implant material, joint articulation simulation, mechanisms for short-term and long-term tissue bonding and attachment, desired surgical procedure, material choices, and the incorporation of any pre-engineered standard elements in the implant.

In some embodiments, FEA mechanical simulations of tissues and the implant are used to optimize the interaction to provide best possible function and minimize stress shielding.

Articulating Joint Simulation, 3.6: In some embodiments, the implant and surgical procedure at or near an articulating joint in the body of a subject (e.g. hip or knee). In some embodiments, it is necessary to simulate the function of a joint at or near the implant site. Computational analysis provides an assessment of joint range of motion, joint strength, joint durability, etc.

Finite Element Analysis, 3.7: In some embodiments, Finite element analysis (FEA) is performed. FEA is a computer simulation technique in which the object is represented by a geometrically similar model consisting of multiple, linked, simplified representations of discrete regions or finite elements on an unstructured grid. See, for example, Finite Element Methods for Structures With Large Stochastic Variations, Elishakoff, 1. and Ren, Y, 2003; Finite Element Methods With B-Splines, Hollig, K., 2003. Standard elements may include articulation components (such as the ball and socket of a prosthetic hip joint), joinery to enable multiple sections of an implant to be assembled and attached during the surgical procedure, and design features to enable the device to be adjusted in size or shape during the initial implantation and at a future time post-implantation, if desired. FEA provides a mathematical method to solve the limitations of the implant based on the geometric design and material type used.

Table 2 outlines the methodology for FEA simulation.

| | |
|---|---|
| 1 | Identify possible bone conditions from medical imaging |
| 2 | Import solid model(s) (e.g., .igs or .stp file format) |
| 3 | Assign material properties |
| 4 | Define connectivity between solid models |
| 5 | Define fixed regions, other known displacements and boundary conditions |
| 6 | Define known loads based on activity level |
| 7 | Select mesh element type and size |
| 8 | Mesh convergence study |
| 9 | Define linear or non-linear solution type |
| 10 | Define required output variables |
| 11 | Solve |
| 12 | Assess results |
| 13 | Identify functional changes or capabilities based on results |

In some embodiments, pre- and post-operative clinical and biomechanical assessments will be made for functional assessment of the personalized implants. Clinical evaluations include joint range of motion and strength testing. For biomechanical assessment FEA simulations will be used to develop geometric CAD solid models with the implant in-situ through virtual surgical operation simulating the actual surgery done to the subject. A number of 3D elements (e.g.

tetrahedral, hexahedral, wedge or some combination thereof) are used to create finite element meshes of the geometric models. Mesh convergence analysis is conducted for accurate simulations. Various loading conditions as obtained from the literature and pre- and post-operative functional testing of the subject are tested to predict stress localization in the interface and stress shielding. Model parameters are obtained from the image data and material testing of biopsy specimens harvested during surgery. A linear static analysis is conducted to obtain solutions. As needed, more sophisticated analysis such as nonlinear and transient analyses is conducted to reflect the level of physical activities of the subject. The simulation results are cross-validated with those from the pre- and post-operative functional testing and further biomechanical assessments are done accordingly.

In some embodiments, based on the results of the FEA and joint articulation, the Device fixation an or Device design may need to be updated. Once the design is validated through the previous simulations, the CAS programming can be generated (and/or updated) and the design rationale will be presented to the surgeon in a collaborative design session that can be performed remotely.

CAS Offline Programming, 3.8: In some embodiments, the computer assisted surgical (CAS) system is programmed offline. The CAS program references the resection geometry. The CAS robotic resectioning process is verified using a virtual 3D model of patient anatomy. Robotic surgery is simulated for the resection profile. Optimum location for bone removal, edge smoothing, and hole cuts are all matched to the device design.

Example IX

Pre-Surgical Collaboration

Second Embodiment

Figure 13:
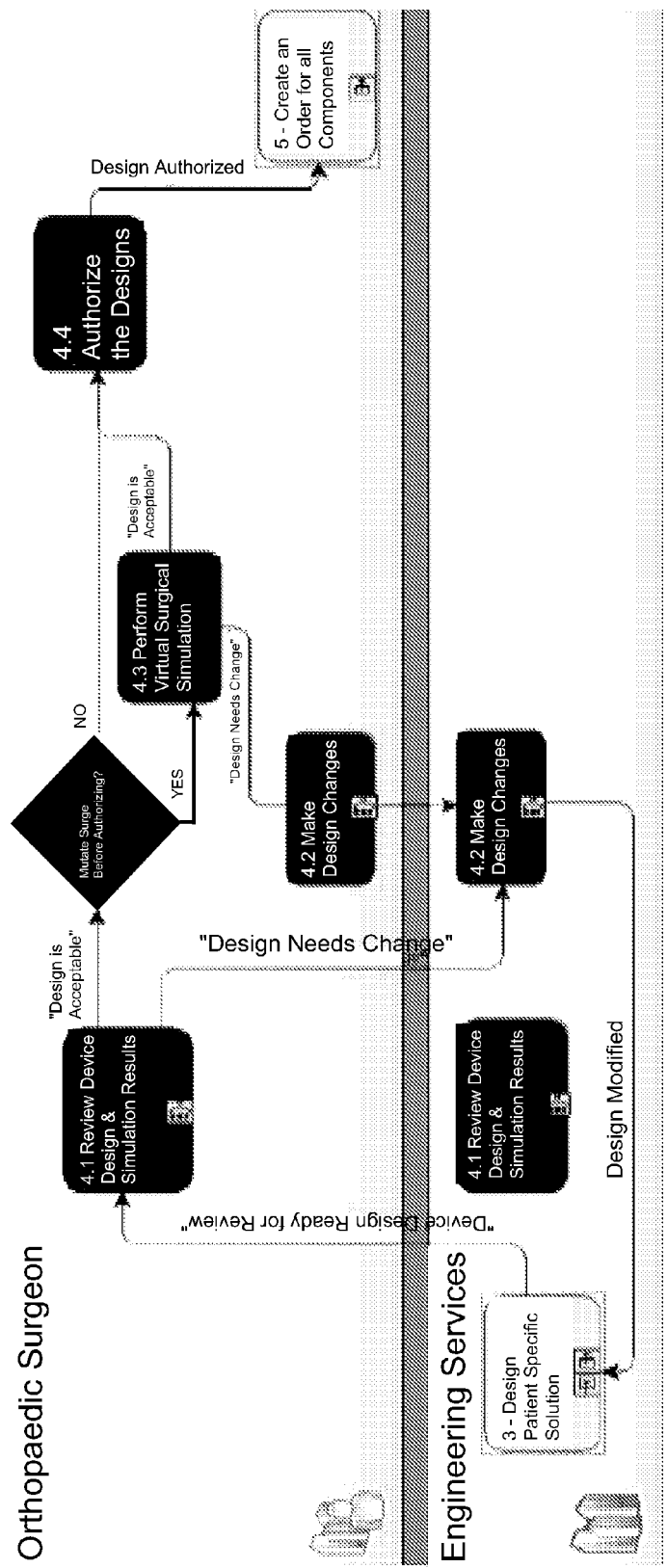
FIG. 13 illustrates a detailed schematic of one method of design collaboration with clinicians according to some embodiments as illustrated in FIG. 10 (Second Embodiment of invention).

In some embodiments, using the methods and technology described herein and based on FIG. 13, the designed components are collaboratively reviewed and authorized for production. The surgeon reviews the preliminary design and makes modifications if desired. If modifications are made, simulations (FEA, articulating joint and CAS) are repeated to validate the implant. Once the surgeon authorizes the component designs, then an order for all required components can be created.

Review Device Design and Simulation Results, 4.1: In some embodiments, the surgeon makes clinical evaluations in the collaborative design session to determine the desired morphology of areas to be resectioned and an initial determination is made of how an implant will be shaped to make the necessary repair. Additional clinical data may also be used in this determination, as appropriate based on the best possible medical practice. The surgeon, through the haptics graphical user interface is able to offset the RRP by a constant or variable offset of the RRP variably based on his/her discretion.

In some embodiments, additional clinical information includes subject history for relevant parameters including a complete medical history with emphasis on factors that alter strength of tissues such as general health, anthropometric measures such as height and weight, activity, skeletal and connective tissue health factor including bone density, and others that are critical for application. (FIG. 3A-3D).

In some embodiments, the transfer of information to and from surgeon is performed with a virtual 3D digital model of subject data that is calibrated for image spatial/spectral resolution and processed to accurately replicate the physical dimensions of the subject-specific anatomical structures.

Make Design Changes, 4.2: In some embodiments, this step includes all the capabilities of Steps 3.4 and 3.5. This dataset is transmitted electronically to the clinician who is able to manipulate the digital model dynamically in order to view any necessary aspect of the structure. Using virtual collaboration software, the surgeon then marks the area for any necessary clinical manipulation such as excision, and labels additional areas such as desirable locations for attachment of the prosthetic, regions that must be left alone, and provides other annotations regarding the surgical procedure and factors that should be addressed in the design of the final implant. This data is then communicated, digitally in some embodiments, back to the manufacturing firm where further evaluation and design is performed.

Perform Virtual Surgical Simulation, 4.3: In some embodiments, the implant design is evaluated by the clinician using virtual 3D presentation methods and/or solid models as illustrated in FIGS. 3A-3D and 4A-4D. Fit is checked, methods of attachment to healthy tissues are evaluated, methods of assembly of implant components (if multiple components) are evaluated, and the entire surgical procedure is performed "virtually" using 3D display and related methods and/or with solid models. If required, steps 3 and 4 shown in TABLE 2 and simulations are repeated until a final digital design and surgical plan are made and the surgeon and engineers approve the design.

Authorize the Designs, 4.4: In some embodiments, both the device and the procedures are authorized. After authorization, an order is created that leads to the production of all Device components and an optional physical model for patient education.

Example X

Produce Device Components

Second Embodiment

Figure 14A:
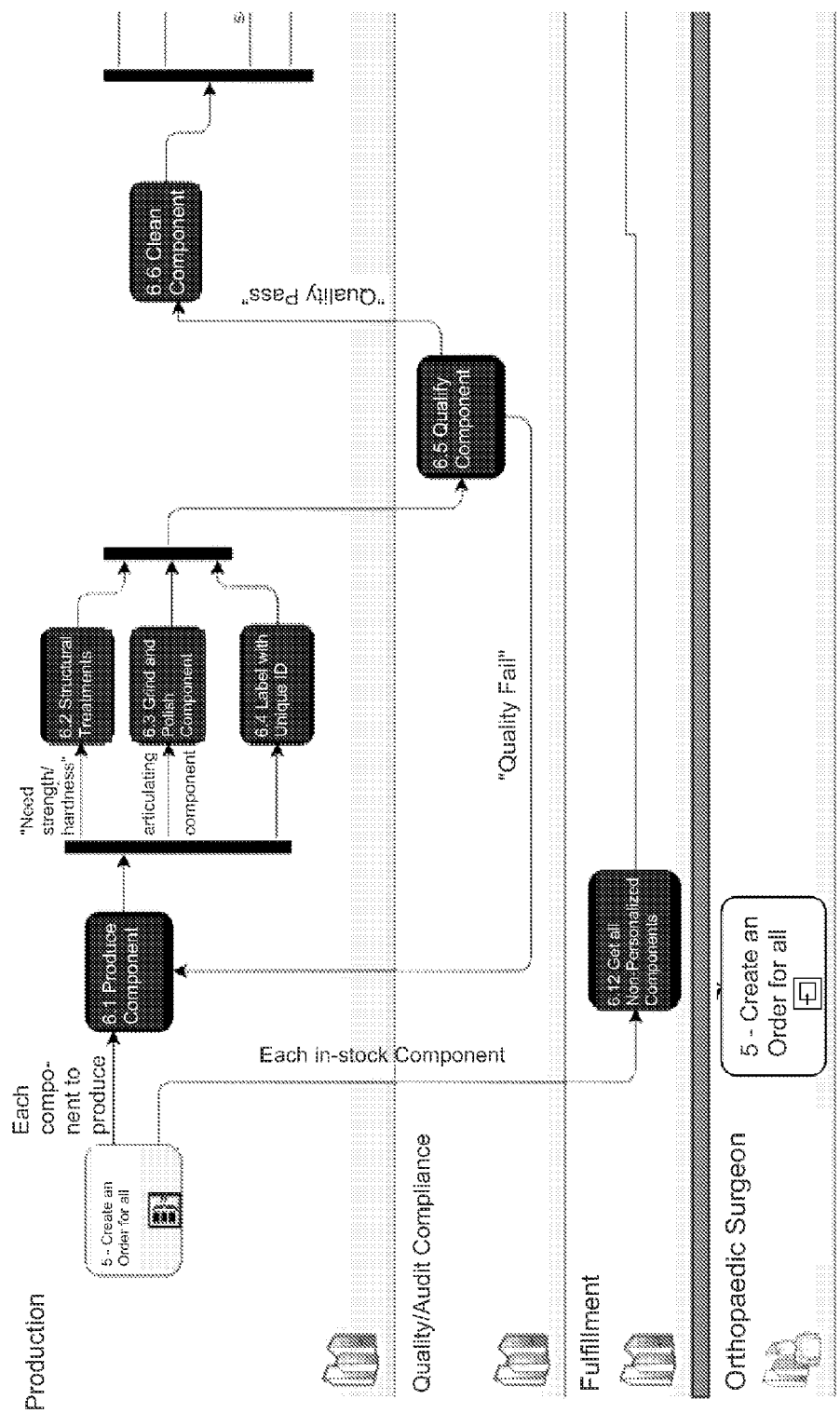
FIGS. 14A and 14B illustrate a detailed schematic of one method of producing device components according to some embodiments as illustrated in FIG. 10 (Second Embodiment of invention).
Figure 14B:
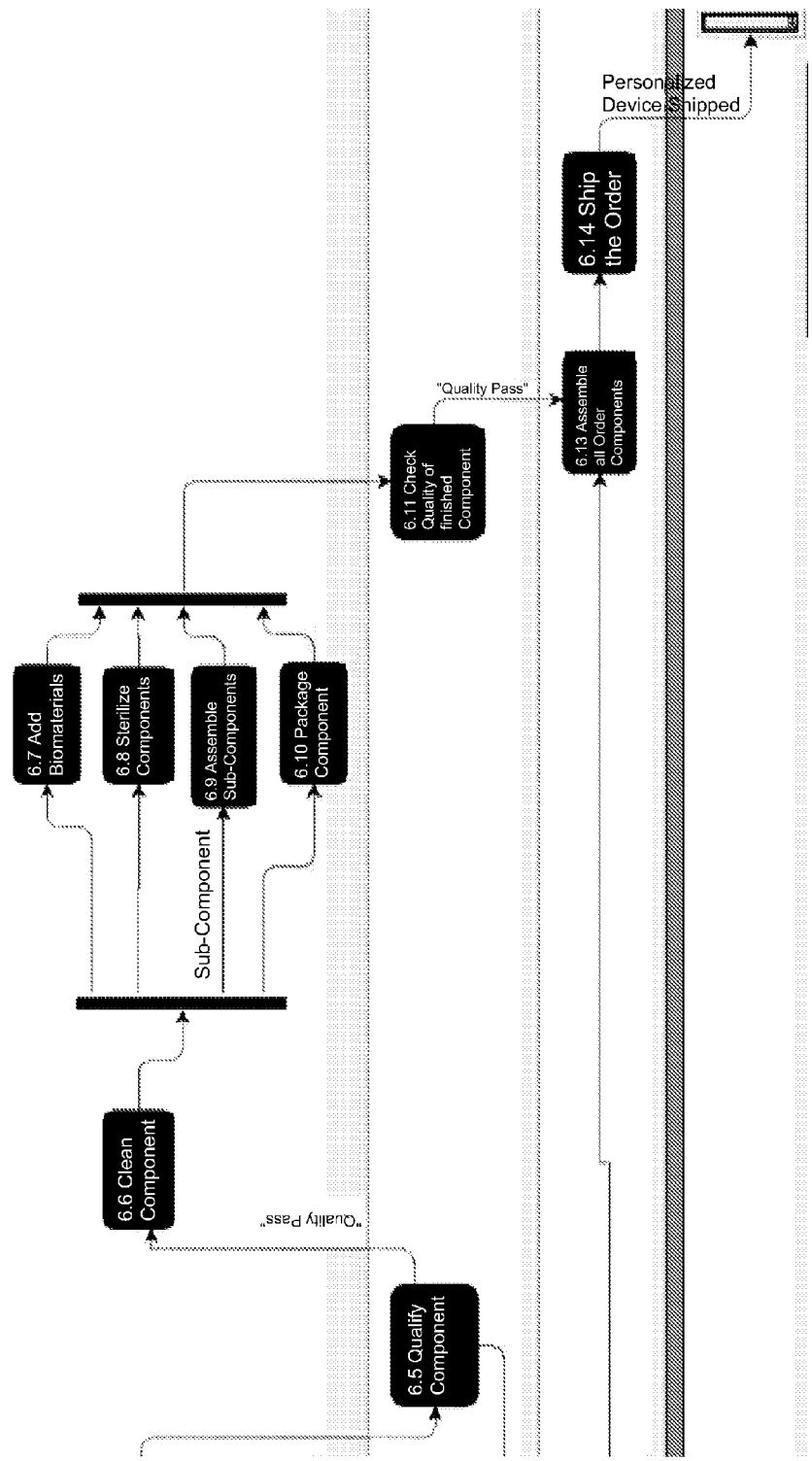

In some embodiments, using the methods and technology described herein and based on FIGS. 14A and 14B, a patient-specific solution is produced.

In some embodiments, the firm manufactures a personalized implant in 48 hours or less. Additive manufacturing technology is used to produce a near-net-shape implant, a tool path program is created using the authorized implant shape, the five-axis finishing operation program is proved out virtually using simulation, multi-axis grinding and polishing machines manufacture the implant, and nearly all hand or manual labor is eliminated as well as associated costs. Dimensions are then verified and finish quality is confirmed, the implant is cleaned and biomaterials are added, and the implant is sterilized, packaged and shipped to surgeon.

In some embodiments, the term Device has referred to the primary device to be implanted (e.g., hip, knee) but typically includes the collection of all Device Components. A Component could be the Device (e.g., trauma plate), or a part of a Device (e.g., ball and socket), or a surgical tool (e.g., Cutting Tool) or other part (e.g., Screw) used to implant the Device.

Produce Component, 6.1: In some embodiments, each component of the Device designed and authorized is produced using additive manufacturing technology. Production of each component is performed with the desired material or materials directly from powdered metals (and certain other materials) that are delivered to the desired spatial location and then laser annealed in place (using, for example, DMD, LENS or the like) or annealed using an electron beam (EBM). This produces a very high strength fine-grain structure, enables the production of internal features, enables layers of multiple materials, gradients of material properties, inclusion of ancillary internal elements, and produces resultant structures that generally require minimal post-production processing.

In some embodiments, multiple materials are applied sequentially, regionally, and in designated locations, if required to achieve desired properties For example, the bone interface aspect of a bulk Ti6Al4V ELI implant can be produced with cpTi to enhance bone bonding, or a gradient of materials may be created to affect galvanic processes.

In some embodiments, Nitinol shape-memory alloy structures can be entirely Ti on the surface to minimize Ni toxicity.

In some embodiments, and as desired during the additive manufacturing approach, the process may be stopped and an element may be added, followed by continued additive processing. Such elements can include functional sensors such as MEMS devices including, but not limited to, neuronal, neuromuscular or skeletal stimulators, optical elements such as lens, structural elements such as ceramic whiskers, or other elements to provide functional or other capabilities. Any material or device can be incorporated that is not damaged by the thermal, optical and other constraints posed by the laser or electron additive manufacturing process, and in consideration of the laser or electron additive manufacturing process resolution limits.

In some embodiments, volume is added automatically for production so that a higher tolerance surface can be created from grinding away the extra volume into the originally designed shape, per step 6.3.

Structural Treatments. 6.2: In some embodiments, Additional processing such as ion beam implantation or annealing may also be performed. The surface texture resolution of the additive manufacturing process is currently ~10 µm with no rough or abrupt transitions. It is thus intrinsically suitable for many tissue interfaces without further processing. For example, this texture limit can enable the direct production of tissue interfaces with features that may be as small as 10 µm, or larger features as desired in order to enhance tissue interactions such as bone growth into the implant. Other post-production processes include ion beam implantation, as is routinely used to harden bearing surfaces in prosthetic knees and hips, as well as annealing and other thermal treatments to effect material structure.

Grind and Polish Component, 6.3: In some embodiments, post-production processes include subtractive manufacturing processes for finish machining operations, grinding and polishing as may be required for joining surfaces and for bearing surfaces, such as in articulation joints, etc. The grinding/polishing makes the precision of the surface higher than just from Additive Manufacturing, but this step may not be required when the component does not have an articulating joint surface.

Label with Unique ID, 6.4: In some embodiments, a component is etched or otherwise labeled or tagged with a unique ID for further tracking through the process and during long-term monitoring and/or post-revision evaluation.

Qualify Component, 6.5: In some embodiments, each Device Component is checked to ensure that the Shape and Structure from Production, as well as all post-production operations meet the required levels of quality. Any component that fails this quality check will be sent back through the previous process steps for correction or re-production.

Clean Component, 6.6: In some embodiments, quality of a medical implant device depends on the proper cleaning of the device during processing. Residue-free implants are help to reduce rejection due to insufficient surface quality. Contaminants can cause patients pain and inflammation and may lead to implant failure. In some embodiments, the present invention provides any cleaning procedure suitable for yielding contaminant-free and residue-free device components including for example one or more of sterilization, ultrasonic cleaning, chemical treatments (e.g., decontaminating agent, detergent, etc.), high pressure treatment, high temperature treatment, abrasion, ion beam cleaning, combinations thereof, etc.

Add Biomaterials, 6.7: In some embodiments, biomaterials will be added to the orthopedic device. These biomaterials will stimulate bone growth and/or provide drug eluting functionality. In some embodiments, these biomaterials will be stem cells and in others they will be antibiotics.

Sterilize Components, 6.8: In some embodiments, the components are sterilized. In some embodiment, any suitable method may be used to sterilize the components. In some embodiments, gamma ray irradiation is used to sterilize the components. In some embodiments, this step may happen before or after packaging. In some embodiments a gamma ray irradiation facility is used for mass sterilization of medical device components.

Assemble Sub-Components, 6.9: In some embodiments, multiple components will need to be combined (assembled) to make up a single multi-part component.

Package Component, 6.10: In some embodiments, the components are packaged to protect the component from the harshness of the shipping process, to maintain cleanliness, and to assure a sterilized component is received by the customer. In some embodiments, each component is packaged separately. In some embodiments, sub-assemblies (multiple components) are packaged as an assembled medical device.

Check Quality of finished Component, 6.11: In some embodiments, the quality of the components will be checked. In some embodiments, this is a geometrical feature check used to assure dimensional or surface integrity. In some embodiments this is a check of the quantity of biomaterials application and processing.

Get all non-personalized Components, 6.12: In some embodiments, components are required that do not have to be 'produced' specifically for this order and are likely either acquired or pulled from inventory. The production or ordering of these non-personalized components is part of a separate process.

Assemble all Order Components, 6.13: In some embodiments, all components of the order need to be collected together to complete the Order and prepare for shipping. This activity includes both company-produced personalized components as well as all non-personalized components from inventory.

Ship the Order, 6.14: In some embodiments, all device components need to be shipped to the appropriate location, ensuring that they arrive within the agreed timeframe. Shipping details are provided to the appropriate surgeon and facility.

Example XI

Long-Term Monitoring

Second Embodiment

In some embodiments, using the methods and technology described herein, the patient-specific solution is monitored throughout the device's active use and, where applicable, upon revision of the device.

In some embodiments, after some time for healing, periodic evaluations are made by a variety of clinicians. This may include orthopedic surgeons, radiologists, physical therapists or some combination of these professionals. These professionals periodically send updates to the engineers. The engineers include the results in the patient registry to document success rates. A registry tracks the patient progress over the life of the patient. It will also be used for reference in future device designs. In some embodiments, the registry comprises a database that is referenced by the case-based expert systems utilized in preliminary device design. The patient profile information is also used for further joint articulation simulations to validate the simulation methodology.

What is claimed is:

1. A system for personalizing a biocompatible device, comprising:
    a subject profile and associated case number for a patient;
    a scanner for acquiring medical imaging for the subject profile;
    a design/manufacturing team for receiving the subject profile and the associated case number for producing a virtual 3D design model; and
    a biocompatible device produced by referencing the 3D design model.

2. The system of claim 1, wherein the subject profile includes:
    Medical diagnosis of the subject, subject-specific medical imaging, anthropometric data, whole body virtual 3D model for motion simulation and genomic data.

3. The system of claim 1, wherein said scanner is selected from at least one of: CT(computed tomography), MRI(magnetic resonance imaging), PET(positron emission tomography), digital X-ray, and ultrasound.

4. The system of claim 1, wherein the virtual 3D design model includes an implant design developed from at least one of:
    CAD(computer-aided design), CAM(computer aided manufacturing), FEA(finite element analysis) of biological tissue of the subject, FEA of materials, joint articulation simulation, or whole body motion simulation.

5. The system of claim 1, further comprising:
    a case-based reasoning expert system data base used for case-by-case system learning, for correlating simulation forecasting to actual said subject results and for presenting timely intelligent information to the design/manufacturing team commencing the preliminary design event of the virtual 3D design model.

6. The system of claim 1, further comprising:
    a virtual, remote and real-time collaboration event between the design/manufacturing team and additional Medical personnel to review, validate and authorize a final virtual 3D design model of said subject.

7. The system of claim 1, further comprising:
    a hybrid model to validate said virtual 3D design model and the integrity of the biological interface in a said subject using a subject-specific biocompatible device 3D CAD model and a whole body motion simulation virtual 3D model; and
    an articulating joint simulation and/or whole body motion simulation;
    a FEA(finite element analysis), wherein said FEA assesses function and expected lifecycle of said personalized biocompatible device based on parameters of subject profile; and
    a virtual reality surgical simulation event using subject whole body virtual 3D model and the virtual 3D design model.

8. The system of claim 1, further comprising:
    a CAS(computer assisted surgery) system being programmed by referencing the associated virtual 3D design model.

9. The system of claim 1, further comprising:
    a light weight 3D physical model produced using 3D printing of said biocompatible device and a mating 3D physical model of the bone of said subject for subject pre-surgical education prior to implant surgery.

10. The system of claim 1, further comprising:
    a biocompatible device produced with additive manufacturing technology, with precision multi-axis grinding and polishing, and validating finished quality and dimensions of said biocompatible device features.

11. The system of claim 1, wherein said biocompatible device is selected from a group consisting of a skeletal orthopedic prosthesis or implant, a dental prosthesis or implant or a soft tissue or hard tissue prosthesis or implant.

12. The system of claim 1, further comprising:
    a haptics physical/graphical user interface for virtual and dynamic examining, design feature modifying and authorizing of the virtual 3D design model, wherein if modifications by feature changes to the virtual 3D design are made, revalidation of the final design is executed using a hybrid model simulation consisting of finite element analysis and articulating joint/whole body motion simulation, surgical simulation, and/or CAS (computer assisted surgery) simulation.

13. A method for personalizing surgical instruments or instrumentation, comprising the steps of:
    generating a subject profile and associated case number of a target surgeon;
    transferring the subject profile and associated case number to a design/manufacturing team;
    producing a virtual 3D design model of instrument referencing subject surgeon; and
    producing a surgical instrument device or instrumentation that is configured to the subject profile including hand geometry, range of motion and upper body strength.

14. The method of claim 13, wherein the subject profile includes:
    subject-specific imaging, anthropometric data, whole body virtual 3D model for motion simulation and genomic data of the surgeon.

15. The method of claim 13, wherein the transferring step includes the step of:
    transferring the subject profile and the associated case number to a design/manufacturing team to commence a preliminary virtual 3D design modeling event before the virtual 3D design model is produced.

16. The method of claim 13, further comprising the step of:
    a case-based reasoning expert system data base for case-by-case system learning, for correlating simulation forecasting to actual said subject results and for presenting timely intelligent information to the design/manufacturing team commencing the preliminary design event of the virtual 3D design model.

17. The method of claim 13, further comprising the step of:
    providing a virtual, remote and real-time collaboration event between the design/manufacturing team and additional Medical personnel to review, validate and authorize a final virtual 3D design model of said subject.

18. The method of claim 13, further comprising the step of:
    providing a haptics physical/graphical user interface for a said surgeon virtual and dynamic examining, design feature modifying and authorizing the virtual 3D design model which triggers to release to production for surgical instruments or instrumentation.

19. The method of claim 13, further comprising the step of: wherein if modifications by feature changes to the virtual 3D design are made, revalidation of the final design is executed using a hybrid model simulation consisting of finite element analysis and articulating joint/whole body motion simulation, surgical simulation, and/or CAS (computer assisted surgery) simulation.

* * * * *

UNITED STATES PATENT AND TRADEMARK OFFICE
CERTIFICATE OF CORRECTION

PATENT NO. : 8,775,133 B2  
APPLICATION NO. : 13/874948  
DATED : July 8, 2014  
INVENTOR(S) : James Schroeder Page 1 of 1

It is certified that error appears in the above-identified patent and that said Letters Patent is hereby corrected as shown below:

On the title page, item(s) (71) & (72),

The residential city and state for inventor should list Waukesha, WI.

Signed and Sealed this  
Fourth Day of November, 2014

Michelle K. Lee  
*Deputy Director of the United States Patent and Trademark Office*